US012570952B2

(12) United States Patent
Xie et al.

(10) Patent No.: US 12,570,952 B2
(45) Date of Patent: Mar. 10, 2026

(54) DEVICES AND METHODS OF PRODUCING TUBULAR SYSTEMS FOR CELL CULTURE

(71) Applicant: Research Foundation for the State University of New York, Albany, NY (US)

(72) Inventors: Yubing Xie, Cohoes, NY (US); Matthew Jorgensen, Albany, NY (US); Sujith Kollampally, Albany, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 372 days.

(21) Appl. No.: 17/153,867

(22) Filed: Jan. 20, 2021

(65) Prior Publication Data

US 2023/0374446 A1 Nov. 23, 2023

Related U.S. Application Data

(60) Provisional application No. 62/963,517, filed on Jan. 20, 2020.

(51) Int. Cl.
| | |
|---|---|
| *C12N 5/00* | (2006.01) |
| *B01L 3/00* | (2006.01) |
| *C12M 1/00* | (2006.01) |

(52) U.S. Cl.
CPC ........... *C12N 5/0068* (2013.01); *C12M 29/00* (2013.01); *C12N 2513/00* (2013.01); *C12N 2537/10* (2013.01)

(58) Field of Classification Search
CPC ... G01N 2021/7779; G01N 2021/7789; G01N 21/253; G01N 21/7746; G01N 21/8507; G01N 2201/0873; C12M 25/14; C12M 29/00; C12N 2501/115; C12N 2513/00; C12N 2533/74; C12N 2537/10; C12N 5/0062; C12N 5/0068; C12N 5/0621
See application file for complete search history.

(56) References Cited

U.S. PATENT DOCUMENTS

| | | | | |
|---|---|---|---|---|
| 5,226,877 A | * | 7/1993 | Epstein | A61L 24/106 |
| | | | | 604/82 |
| 6,629,947 B1 | * | 10/2003 | Sahatjian | A61B 17/12022 |
| | | | | 604/11 |
| 2006/0040340 A1 | * | 2/2006 | Greene | C12M 33/04 |
| | | | | 435/287.1 |
| 2006/0278588 A1 | * | 12/2006 | Woodell-May | G01N 33/491 |
| | | | | 604/82 |
| 2015/0182660 A1 | * | 7/2015 | Nazhat | A61L 27/54 |
| | | | | 425/398 |

(Continued)

*Primary Examiner* — Nathan A Bowers
(74) *Attorney, Agent, or Firm* — Garrett M. Smith

(57) ABSTRACT

The present disclosure relates to devices and methods for forming microfibers, and organoids useful in cell-culture. In embodiments, a method of forming one or more microfibers, includes: flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, wherein the first reservoir, the conduit, and the second reservoir are in fluid communication. In embodiments, the conduit includes one or more needles in fluid communication with the second reservoir.

14 Claims, 25 Drawing Sheets

(56)          References Cited

U.S. PATENT DOCUMENTS

| | | | |
|---|---|---|---|
| 2016/0346427 A1* | 12/2016 | Nunes | .................. A61L 24/0015 |
| 2019/0008606 A1* | 1/2019 | Ahn | ........................... C08J 9/30 |
| 2019/0070339 A1* | 3/2019 | Gerecht | .............. A61L 27/3808 |

* cited by examiner

C. By the end

A. At the beginning

DEVICES AND METHODS OF PRODUCING TUBULAR SYSTEMS FOR CELL CULTURE

CROSS REFERENCE TO RELATES APPLICATIONS

This application claims the benefit of the filing date of U.S. Provisional Application No. 62/963,517 filed 20 Jan. 2020. The content of this earlier filed application is hereby incorporated by reference herein in its entirety.

FIELD OF THE INVENTION

The present disclosure relates to three-dimensional (3D) structures suitable for use in, inter alia, cell culture applications. For example, the present disclosure relates to a device and process for 3D structure formation in various configurations useful in clinical or research settings including cell culture.

BACKGROUND

Hydrogel is a widely used type of biomaterial and typically includes a network of polymer chains with high water content. Hydrogels have wide applications in biomedical fields, including but not limited to, biomaterials for cell culture, scaffolding materials for tissue engineering, controlled release system for drug and gene delivery, and delivery vehicles for cell therapy. A number of naturally occurring hydrogels and synthetic hydrogels already exist. For example, naturally occurring hydrogels include alginate, chitosan, hyaluronic acid, methylcellulose, collagen, gelatin, collagen-containing hydrogel such as MATRIGEL® brand biological cell culture substrate, fibrin, silk fibroin, peptide-based, etc. Synthetic hydrogels include polyethylene glycol (PEG), polyacrylamide, poly(N-isoprolylacrylamide) (pNi-PAAm), poly(acrylic acid), and poly-2-hydroxyethyl methacrylate (PHEMA), etc.

Alginate containing hydrogels are an example of a hydrogel that has found numerous applications in biomedical science and engineering due to its favorable properties, including biocompatibility and ease of gelation. Alginate hydrogels have been particularly attractive in wound healing, drug delivery, tissue engineering, and cell therapy applications to date, as these gels retain structural similarity to the extracellular matrices in tissues and can be manipulated to play several critical roles.

Alginate is a naturally occurring anionic polymer typically obtained from brown seaweed and has been extensively investigated and used for many biomedical applications, due to its biocompatibility, low toxicity, relatively low cost, and mild gelation by addition of divalent cations such as $Ca^{2+}$, $Ba^{2+}$, $Sr^{2+}$, $Zn^{2+}$ and others.

Alginate hydrogels can be prepared by various cross-linking methods, and their structural similarity to extracellular matrices of living tissues allows wide applications in wound healing, delivery of bioactive agents such as small chemical drugs and proteins, and cell transplantation. Alginate hydrogel tubular structures have been fabricated using various technologies such as glass capillary-based coaxial microfluidics, microfluidics through microfabricated nozzle array or micropatterned filter, microfluidic spinning, wet spinning, extrusion, and interfacial complexation. Moreover, core-shell structured alginate hydrogel hollow fibers or microtubes have been fabricated using micro-extruder, needle-based, aluminum-based or glass capillary-based coaxial microfluidics, and microchannel-based microfluidics.

Microfibers or microtubes can be used in versatile fashions, such as: (i) to form cell fibers and organize into higher-order 3D cellular structure; (ii) to generate spatially coded fibers for co-culture; (iii) neutrophil migration and neuron alignment; (iv) to construct smooth muscle-like spring; (v) to assemble micro-scale toroidal cellular modules for building microvascular-like structure; (vi) to create temperature-responsive cell fibers; (vii) to create magnetics-responsive cell fibers; (viii) to produce bacteria cellulose for cell culture; (ix) protein fibers for controlled release; (x) sacrificial microfibers for enhanced nanoparticle-based gene delivery; (xi) automated production of T-cells for future adoptive immunotherapy; (xii) scalable culturing of tumor-initiating cells; (xiii) enabling human pluripotent stem cell (hereinafter, sometimes referred to as: "hPSC") self-renewal and storage; (xiv) high-fold expansion and enhanced stem cell differentiation (e.g., human embryonic stem cell (hereinafter, sometimes referred to as: "ESC") differentiation into liver-like cells); (xv) hPSC differentiation to neural stem cells (hereinafter, sometimes referred to as: "NSCs"); (xvi) adipogenesis of mouse ESCs; (xvii) mouse NSC differentiation to neurons and glial cells; (xviii) endothelial differentiation of mesenchymal stem cells (hereinafter, sometimes referred to as: "MSCs"); (xix) mimicking the ESC-microenvironment to study pluripotent signaling that restricts cancer metastatic potential; (xx) enhancing hepatic function; (xxi) facilitating neural cell alignment; and (xxii) exhibiting biomineralization potential. In-vivo studies have demonstrated: (a) enhanced immune-protection for islet transplantation, (b) normalization of glucose concentration for 13 days using minimally invasive transplantation of 20-cm-long islet cell fiber, and (c) capacity for bone regeneration through 12-week implantation.

The following have been encapsulated in alginate hydrogel microfibers and/or microtubes: (i) stem cells (e.g., ESCs, iPSCs, MSCs, NSCs); (ii) endothelial cells; (iii) smooth muscle cells; (iv) fibroblasts; (v) osteoblasts; (vi) myoblasts; (vii) myocytes; (viii) nerve cells; (ix) epithelial cells; and (x) T cells. However, no report shows to culture lens, retina, or salivary gland cells or organoids.

Thus, there is a need in the art to develop novel and improved devices for fabricating microtubules and mircrostrands optimized for cell culture, which are easy to use, easy to clean, and easy to transfer and transport the microtubule and microstrand products.

SUMMARY

In embodiments, the present disclosure provides a method of forming one or more microfibers, including: flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, wherein the first reservoir, the conduit, and the second reservoir are in fluid communication. In embodiments, the conduit includes a first needle extending from the first reservoir to the second reservoir, wherein the second reservoir is disposed within a syringe having a distal opening, and wherein an adapter is disposed around the first needle and within the distal opening.

In embodiments, the present disclosure relates to a method of forming one or more microfibers, including:

flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, wherein the conduit includes one or more needles, and wherein the first reservoir, the one or more needles, and the second reservoir are in fluid communication. In embodiments, the one or more needles are attached by an adapter to the second reservoir, wherein the one or more needles and second reservoir are in fluid communication.

In embodiments, the present disclosure provides a method of forming a tubular strand comprising bubbles, including: flowing a hydrogel agent through a conduit from a first reservoir to a second reservoir including a crosslinking agent under conditions suitable for forming one or more tubular strands including one or more bubbles within the second reservoir, wherein flowing includes pulling the hydrogel agent from a first reservoir and reagents from a third reservoir into the second reservoir through the conduit, wherein the first reservoir, the second reservoir, the third reservoir and conduit are in fluid communication. In embodiments, reagents disposed within the third reservoir include one or more cross-linking agents in accordance with the present disclosure.

In embodiments, the present disclosure includes an apparatus for forming micro-strands, including: a first reservoir containing a crosslinking agent; a second reservoir containing a hydrogel agent; an adapter to connect the first reservoir and a second reservoir; and a mechanical component to create a vacuum within the first reservoir to transfer one or more units of the hydrogel agent within the second reservoir to the first reservoir.

In embodiments, the present disclosure includes a device for forming one or more organoid structures or one or more microtubules, including: a first reservoir; a second reservoir; a vacuum pump; and an adapter, wherein the first reservoir and second reservoir are in fluid communication via the adapter, and wherein the vacuum pump is configured to pull reagent, when present, from the first reservoir to the second reservoir.

In embodiments, the present disclosure includes a method of forming three-dimensional cell-culture structure, including: flowing a hydrogel agent through a conduit from a first reservoir to a second reservoir including a crosslinking agent under conditions suitable for forming one or more three-dimensional cell-culture structures within the second reservoir, wherein flowing includes pulling the hydrogel agent into the second reservoir through the conduit. In embodiments, the conduit includes one or more needles attached by an adapter, wherein the first needle and second needle are in fluid communication.

In embodiments, the present disclosure relates to a method of forming one or more microfibers, including: flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, and wherein the conduit includes a first needle and second needle attached by an adapter, wherein the first needle and second needle are in fluid communication.

In some embodiments, the present disclosure relates to a method of forming one or more microfibers, including: flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, and wherein the conduit includes a first needle attached by an adapter to the second reservoir, wherein the first needle and second reservoir are in fluid communication.

In some embodiments, the present disclosure includes microfiber products or microtube products formed by the methods of the present disclosure.

In embodiments, the present disclosure includes an apparatus for forming micro-strands or microtubes, including: a first reservoir containing a crosslinking agent; a second reservoir containing a hydrogel agent; an adapter to connect the first reservoir and a second reservoir; a mechanical component to create a vacuum within the first reservoir to transfer one or more units of the hydrogel agent within the second reservoir to the first reservoir.

In some embodiments, the present disclosure relates to a device for forming one or more organoid structures, one or more micro-strands, or one or more microtubes including: a first reservoir; a second reservoir; a vacuum pump; and an adapter, wherein the first reservoir and second reservoir are in fluid communication via the adapter, and wherein the vacuum pump is configured to pull reagent, when present, from the first reservoir to the second reservoir.

In some embodiments, the present disclosure relates to a method of forming a three-dimensional cell-culture structure, including: flowing a hydrogel agent through a conduit from a first reservoir to a second reservoir including a crosslinking agent under conditions suitable for forming one or more three-dimensional cell-culture structures within the second reservoir, wherein the flowing includes pulling the hydrogel agent into the second reservoir through the conduit, and wherein the conduit includes a first needle and second needle attached by an adapter, wherein the first needle and second needle are in fluid communication.

These and other aspects of the present disclosure are realized in an improved device and methods of making microtubules and microstrands useful in cell culture, as shown and described.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

FIG. 5B is a cross-sectional side view of a conduit in accordance with the present disclosure with an adapter. FIG. 5C is a cross-section side view of an adapter embodiment of the present disclosure. FIG. 5D depicts another syringe-in-syringe apparatus with needle-in-needle apparatus of the present disclosure. FIGS. 5E and 5F depicts conduits of the present disclosure including one or more needles within one or more needles.

FIG. 6B is a cross-sectional side view of a conduit in accordance with the present disclosure with an adapter. FIG. 6C is a cross-section side view of an adapter embodiment of the present disclosure.

Figure 1A:
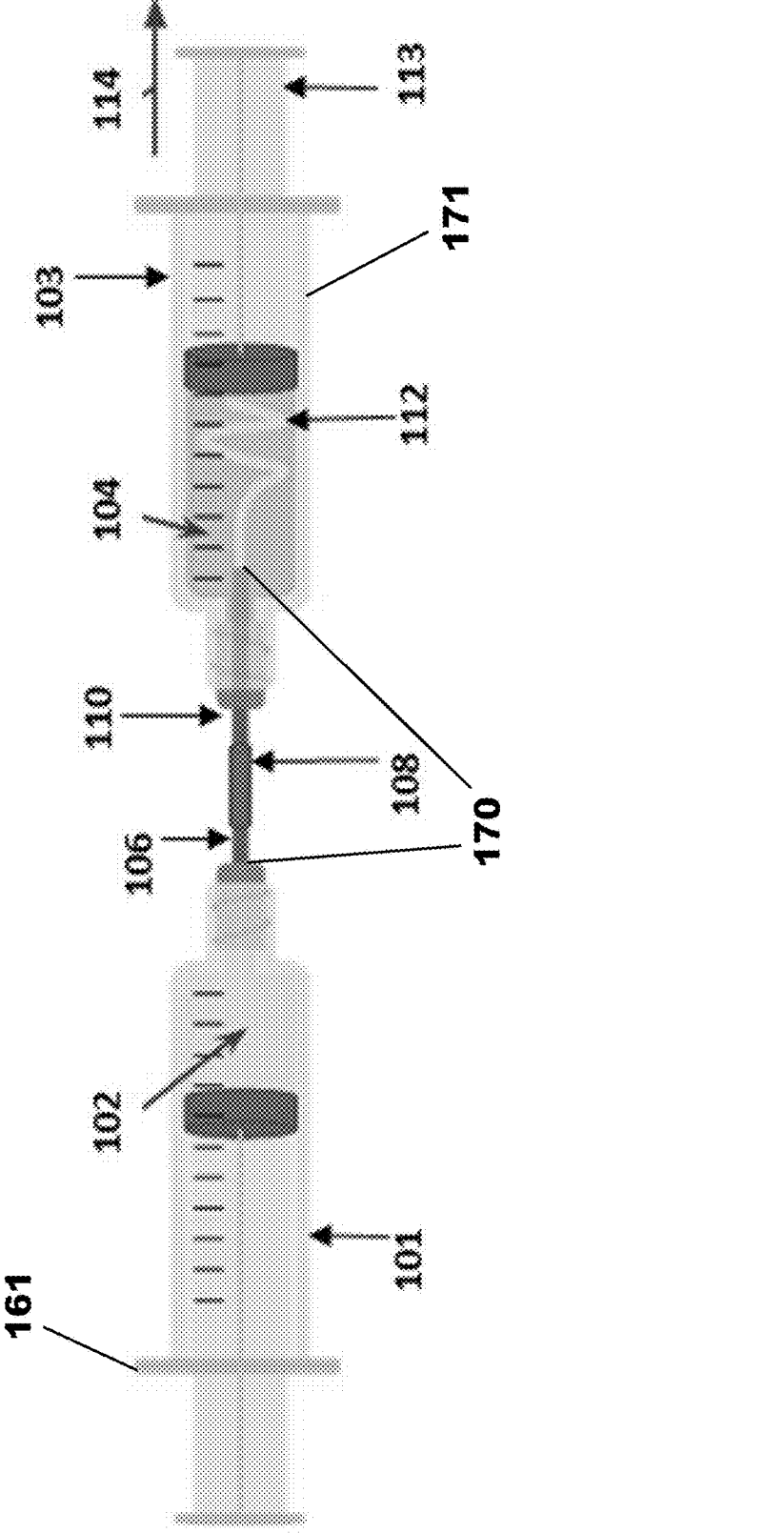
FIGS. 1A and 1B are diagrams of syringe-in-syringe devices in accordance with embodiments of the present disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

The present disclosure is directed towards devices, microfibers, microtubules, and methods of forming one or more microfibers or microtubules. For example, in embodiments the present disclosure includes a method of forming one or more microfibers, including: flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, wherein the first reservoir, the conduit, and the second reservoir are in fluid communication. In another example, the present disclosure includes a method of forming one or more microfibers including: flowing a hydrogel agent through a conduit from a first reservoir to a second reservoir include a crosslinking agent under conditions suitable for forming one or more microfibers within the second reservoir, wherein the flowing includes pulling the hydrogel agent into the second reservoir through the conduit, and wherein the conduit includes a first needle and second needle attached by an adapter, wherein the first needle and second needle are in fluid communication.

Embodiments of the present disclosure may include one or more of the following advantages: (i) user-friendly; (ii) cost effective; (iii) reproducible; (iv) high handleability; (v) high density cell culture; (vi) long term cell culture; (vii) quick cell release; (viii) direct cell storage; and/or (ix) applicable to a wide range of cell types for 3D cell culture, such as: (a) stem cells, (b) healthy cells, (c) diseased cells, and (d) cancer cells.

Definitions

As used in the present specification, the following words and phrases are generally intended to have the meanings as set forth below, except to the extent that the context in which they are used indicates otherwise.

As used herein, the singular forms "a", "an", and "the" include plural references unless the context clearly dictates otherwise. Thus, for example, references to "a compound" include the use of one or more compound(s). "A step" of a method means at least one step, and it could be one, two, three, four, five or even more method steps.

The term "about", as used herein, refers to +/−10% of the stated value or a chemical or obvious equivalent thereof.

As used herein the term "alginate" refers to an alginic acid or a salt of alginic acid such as sodium, calcium, barium, or strontium salt of alginic acid. In some embodiments, the term includes but is not limited to algin, alginic acid, alginate acid, alginic acid sodium salt, sodium alginate, etc.

As used herein the term "alginic acid" or "algin" refers to an insoluble gelatinous carbohydrate in many brown seaweeds. In embodiments, alginic acid includes D-mannuronic acid and L-guluronic acid connected with alpha 1, 4 bonds. In embodiments, alginic acid refers to an insoluble colloidal acid, $(C_6H_8O_6)_n$, found in the cell walls of various kelps.

Detailed Description of Certain Embodiments

In embodiments, the present disclosure includes a method of forming one or more microfibers, including: flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, wherein the first reservoir, the conduit, and the second reservoir are in fluid communication. In embodiments, the conduit includes a first needle extending from the first reservoir to the second reservoir, wherein the second reservoir is disposed within a syringe having a distal opening, and wherein an adapter is disposed around the first needle and within the distal opening. In embodiments, the conduit includes a first needle and second needle attached by an adapter, and wherein the first needle and second need are in fluid communication. In embodiments, the adapter is disposed over and atop the first needle, and when present, a second needle. In embodiments, pulling includes moving a plunger disposed within a syringe away from the adapter under conditions sufficient to form a vacuum. Some embodiments further include positioning a filter in an opening of the conduit within the second reservoir, wherein the filter comprises a plurality of holes. Some embodiments further include, prior to flowing the hydrogel agent, filling the first reservoir with a hydrogel agent, and filling the second reservoir with a crosslinking agent. In embodiments, the first reservoir is disposed within a first syringe and the second reservoir is disposed within a second syringe. In embodiments, the conduit is in fluid communication with a third reservoir including one or more crosslinking agents, and wherein the conduit further comprises a third needle attached to a first needle and a second needle by an adapter, wherein the first needle, second needle, and third needle are in fluid communication.

In embodiments, the present disclosure includes a method of forming one or more microfibers, including: flowing a hydrogel agent through a conduit from a first reservoir to a second reservoir including a crosslinking agent under conditions suitable for forming one or more microfibers within the second reservoir, wherein flowing incudes pulling the hydrogel agent into the second reservoir through the conduit, wherein the conduit includes one or more needles, and wherein the first reservoir, the one or more needles, and the second reservoir are in fluid communication. In embodiments, the one or more needles are attached by an adapter to the second reservoir, wherein the one or more needles and second reservoir are in fluid communication. In embodiments, the second reservoir is a container configured to pull hydrogel agent from the first reservoir to the second reservoir by a vacuum. In embodiments, the conduit extends into a container, and wherein a distal end of the conduit includes a filter comprising a plurality of holes.

In some embodiments, the present disclosure includes a method of forming a tubular strand including bubbles, including: flowing a hydrogel agent through a conduit from a first reservoir to a second reservoir including a crosslinking agent under conditions suitable for forming one or more tubular strands including one or more bubbles within the second reservoir, wherein flowing includes pulling the hydrogel agent from a first reservoir and reagents from a third reservoir into the second reservoir through the conduit, wherein the first reservoir, the second reservoir, the third reservoir and conduit are in fluid communication. In embodiments, the conduit includes a first needle from the first reservoir to the second reservoir, and a second needle form the third reservoir to the second reservoir, wherein the second needle is disposed within the first needle.

Certain embodiments, of the present disclosure include a microfiber product or a microtubule product made by a method in accordance with the present disclosure.

In embodiments, an apparatus for forming micro-strands, includes: a first reservoir containing a crosslinking agent; a second reservoir containing a hydrogel agent; an adapter to connect the first reservoir and a second reservoir; and a mechanical component to create a vacuum within the first reservoir to transfer the hydrogel agent within the second reservoir to the first reservoir. In embodiments, the first reservoir and second reservoir are in fluid communication via a conduit. In embodiments, the conduit includes a first needle disposed within a second needle. In embodiments, the conduit includes a second needle disposed within a first needle, and a third needle disposed within the second needle.

In embodiments, the present disclosure provides a device for forming one or more organoid structures or one or more microtubules, including: a first reservoir; a second reservoir; a vacuum pump; and an adapter, wherein the first reservoir and second reservoir are in fluid communication via the adapter, and wherein the vacuum pump is configured to pull reagent, when present, from the first reservoir to the second reservoir.

In embodiments, the present disclosure relates to a method of forming three-dimensional cell-culture structure, including: flowing a hydrogel agent through a conduit from a first reservoir to a second reservoir including a crosslinking agent under conditions suitable for forming one or more three-dimensional cell-culture structures within the second reservoir, wherein flowing includes pulling the hydrogel agent into the second reservoir through the conduit. In embodiments, the conduit includes one or more needles attached by an adapter, wherein the first needle and second needle are in fluid communication.

In embodiments, the present disclosure relates to a method of forming one or more microfibers, including: flowing a hydrogel agent through a conduit from a first reservoir to a second reservoir including a crosslinking agent under conditions suitable for forming one or more microfibers within the second reservoir, wherein flowing includes pulling the hydrogel agent into the second reservoir through the conduit, and wherein the conduit includes a first needle and second needle attached by an adapter, wherein the first needle and second needle are in fluid communication. In embodiments, the adapter is disposed over and atop the first needle and the second needle. In embodiments, pulling includes moving a plunger disposed within a syringe away from the adapter under conditions sufficient to form a vacuum. In embodiments, the method may further include positioning a filter in an opening of the conduit within the second reservoir, wherein the filter includes a plurality of holes. In embodiments, the process sequence may include, prior to flowing the hydrogel agent, filling the first reservoir with a hydrogel agent, and filling the second reservoir with a crosslinking agent. In embodiments, the first reservoir is disposed within a first syringe and the second reservoir is disposed within a second syringe. In embodiments, the conduit is in fluid communication with a third reservoir including one or more crosslinking agents, and wherein the conduit further includes a third needle attached to the first needle and second needle by an adapter, wherein the first needle, second needle, and third needle are in fluid communication. In embodiments, the conduit is in fluid communication with a fourth reservoir including one or more reagents (such as hydrogel or crosslinking agents of the present disclosure), and wherein the conduit further includes a fourth needle attached to the first needle, second needle and third needle by the adapter, wherein the first needle, second needle, third needle, and fourth needle are in fluid communication.

In some embodiments, the present disclosure relates to a method of forming one or more microfibers, or microtubules including: flowing a hydrogel agent through a conduit from a first reservoir to a second reservoir including a crosslinking agent under conditions suitable for forming one or more microfibers within the second reservoir, wherein the flowing includes pulling the hydrogel agent into the second reservoir through the conduit, and wherein the conduit includes a first needle attached by an adapter to the second reservoir, wherein the first needle and second reservoir are in fluid communication. In embodiments, the second reservoir is a container configured to pull hydrogel agent from the first reservoir to the second reservoir by a vacuum. In embodiments, the conduit extends into the container, and wherein the distal end of the conduit includes a filter including a plurality of holes. In embodiments, the conduit includes a second needle disposed within the first needle, wherein the second needle is in fluid communication with a third reservoir. In embodiments, the first needle is connected to a first syringe, and the second needle is connected to second syringe and wherein the second reservoir is a container. In embodiments, a flow of reagents from the third reservoir are pumped under conditions to form a tubular strand including bubbles.

In embodiments, the processes and devices of the present disclosure are suitable for contacting one or more hydrogel agents of the present disclosure with one or more cross-linking agents of the present disclosure to form one or more micro-strands or microtubules, in accordance with the present disclosure.

In embodiments, the one or more hydrogel agents include hydrogel agent in an amount sufficient to form a micro-strand of a predetermined length or diameter, or a tubular structure having a predetermined length or diameter. Non-limiting examples of suitable hydrogel agents include alginate, and aqueous solutions thereof. In embodiments, an alginate solution includes alginate and water at a concentration of 0.5% to 10% such as 3%, 4%, 5%, 6% percent. In embodiments, the percent as used herein refers to volume percent, used to express the concentration of a solution when the volume of the solute and volume of a solution is given such as wherein volume percent=volume of solute/volume of solution X 100%. In another example, alginate is mixed with water, or alginic acid is combined with a 0.9% NaCl solution. In embodiments, a suitable alginate solution is an aqueous alginate solution with an alginate concentration of 1-20%, 1-15%, 1-10%, about 10%, about 9%, about 8%, about 7%, about 6%, about 5%, about 4%, about 3%, about 2%, or 5%, 4%, 3%, or 2%.

In embodiments, the one or more crosslinking agents of the present disclosure include crosslinking agent in an amount sufficient to crosslink the hydrogel agent of the present disclosure to form a micro-strand of a predetermined length or diameter, or a tubular structure having a predetermined length or diameter. Non-limiting examples of cross-linking agents suitable for use herein include N-hydroxysuccinimide (NHS), ethyl dimethylaminopropyl carbodiimide (EDC), and calcium chloride dihydrate. In some embodiments, the reagents for crosslinking the hydrogel materials were N-hydroxysuccinimide (NHS) from ThermoFisher Scientific (Waltham, MA), ethyl dimethylaminopropyl carbodiimide (EDC), and calcium chloride dihydrate from Sigma-Aldrich.

In embodiments, connective conduits may include a first needle and second needle described below which may each be characterized as having a gauge. As is known in the art, gauge refers to the inner measurement or opening of the needle. Non-limiting examples of needle gauges suitable for use herein include gauges between 10 gauge and 34 gauge, such as e.g., 10-gauge, 15-gauge, 20-gauge, 25 gauge, or 30 gauge.

In embodiments, the methods of the present disclosure include a pulling force or action that creates a vacuum that flows hydrogel agents into the cross-linking agents. In embodiments, a vacuum created is in the amount of 250 to 650 Torr at room temperature or 4 to 37 degrees C. In embodiments, the pull motion 114 may be generated by hand force or that or a machine.

In embodiments, the present disclosure relates to apparatus for forming micro-strands, including: a first reservoir containing a crosslinking agent; a second reservoir containing a hydrogel agent; an adapter to connect the first reservoir and a second reservoir; a mechanical component to create a vacuum within the first reservoir to transfer one or more units of the hydrogel agent within the second reservoir to the first reservoir. In embodiments, the first reservoir and second reservoir are in fluid communication via a conduit. In embodiments, the conduit includes a first needle disposed within a second needle. In embodiments, the conduit includes a second needle disposed within a first needle, and a third needle disposed within the second needle.

In embodiments, the apparatus further includes: (i) a first reservoir as a syringe; (ii) the second reservoir as a syringe; (iii) two syringes of similar gauges, and the needle gauge is varied; and (iv) the needle of the second reservoir syringe that contains the alginate is inserted into the first reservoir syringe via an adapter. In embodiments, the crosslinking agent is a $CaCl_2$) solution. In embodiments, the hydrogel agent is an alginate solution. In embodiments, the hydrogel agent of the second reservoir is an alginate solution with an alginate concentration of 1-10%, such as 3-10%, or 6%, or 3%. In embodiments, the hydrogel agent is an alginate solution which contains alginate with a suitable concentration such as about 6% and one or more of the following materials, including: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; and (xvii) vaccines.

In embodiments, the hydrogel agent is an alginate solution which contains alginate with a suitable concentration such as about 3% and one or more of the following materials, including: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; and (xvii) vaccines.

In embodiments, the mechanical component is a plunger. In embodiments, the crosslinking agent is a $CaCl_2$) solution, or a solution of $CaCl_2$) and polylysine. In embodiments, the first reservoir is a syringe and the second reservoir is a syringe, and the first reservoir syringe has a larger gauge than the second reservoir syringe. In embodiments, the adapter is configured to measures flow rate, controls flow rate, measures pressure, and/or control pressure. In embodiments, the adapter tightly seals the containers or reservoirs or syringes, to enable the creation of a vacuum inside the first container or reservoir or syringe, when the plunger is pulled or when the vacuum is turned on.

In embodiments, the adapter further includes one or more of the following features or abilities: (i) measuring flow rate; (ii) changing flow rate; (iii) measuring pressure; (iv) changing pressure; (v) measuring flow rate of the hydrogel agent in the second reservoir; (vi) changing flow rate of the hydrogel agent in the second reservoir as the hydrogel agent flows to the first reservoir; (vii) measuring pressure within the first reservoir; (viii) measuring pressure within the second reservoir; (ix) changing pressure within the first reservoir; (x) changing pressure within the second reservoir; and (xi) measuring the vacuum within the first reservoir.

In embodiments, the present disclosure includes to a device for forming one or more organoid structures or one or more micro-strands, including: a first reservoir; a second reservoir; a vacuum pump; and an adapter, wherein the first reservoir and second reservoir are in fluid communication via the adapter, and wherein the vacuum pump is configured to pull reagent, when present, from the first reservoir to the second reservoir.

In embodiments, the present disclosure includes a method of forming three-dimensional cell-culture structure, including: flowing a hydrogel agent through a conduit from a first reservoir to a second reservoir including a crosslinking agent under conditions suitable for forming one or more three-dimensional cell-culture structures within the second reservoir, wherein the flowing includes pulling the hydrogel agent into the second reservoir through the conduit, and wherein the conduit includes a first needle and second needle attached by an adapter, wherein the first needle and second needle are in fluid communication. In embodiments, the first reservoir is a syringe, and the second reservoir is a container. In embodiments, the first reservoir is connected horizontally to the second reservoir. In embodiments, the vacuum pump is connected vertically to the second reservoir. In embodiments, the first reservoir is connected to the second reservoir via a vacuum sealed adapter. In embodiments, the device further includes one or more of the following: (i) a connection of a first reservoir horizontally to a second reservoir via an adapter; (ii) a vacuum pump connected to the second reservoir vertically; (iii) a control to set the vacuum pressure applied to the apparatus; (iv) a monitor for monitoring the vacuum pressure applied to the apparatus; (v) a configuration for adjusting the vacuum pressure applied to the apparatus; (vi) and a second reservoir configured for transferring the contents of a first reservoir to a second reservoir by vacuum pressure applied vertically to the second reservoir; and (vii) a filter for filtering the contents of the first reservoir as the contents are transferred to the second reservoir via a porous filter to create one or more (such as a plurality) of micro-strands within the second reservoir. In embodiments, the crosslinking agent is calcium chloride, or derivative thereof. In embodiments, the hydrogel agent comprises alginate. In embodiments, the first reservoir includes alginate and at least one of the following substances, cells; tissues; organoids; micro-organisms; virus; macromolecules; proteins; DNA; RNA; lipids; polysaccharides; exosomes; biocatalysts; pharmacological agents; drugs; genes; vaccines, or combinations thereof. In embodiments, the first reservoir includes alginate and one of: cells, tissues, organoids, or micro-organisms. In embodiments, the first reservoir includes alginate and at least one organoid structure such as a lentoid, spherical lentoid, or substantially spherical lentoid.

Embodiments of the present disclosure include a vacuum driven method to form alginate hydrogel tubular structures to culture stem cells, 3-dimensional lentoid bodies, organoids, and/or other substances in a three-dimensional microenvironment. Tubular structures could include one or more of the following, such as: microfibers, micro-strands, micro-ribbons, micro-strings, microtubes, core-shell hollow fibers, etc. In embodiments, the tubular structures may be formed using a syringe-in-syringe apparatus of the present disclosure or syringe-in-container apparatus of the present disclosure that creates a vacuum to create microtubular structures that include a crosslinking agent, hydrogel agent, and one or more substances of interest. Non-limiting examples of substances of interest may include cells, tissue, organoids, microorganisms, virus, macro-molecules (e.g., proteins, DNA, RNA, lipids, polysaccharides), exosomes, biocatalysts, and/or pharmacological agents (e.g., drugs, genes, vaccines). The tubular structures may be useful in applications, such as: 3D cell culture, 3D printing, scaffolding technology, cell encapsulation, stem cell technology, tissue engineering, cell therapy, controlled release, drug delivery, gene delivery, vaccine, cryopreservation, fermentation, and/or biocatalysts.

Cell culture provides valuable information for understanding biology and pathophysiology. However, cells cultured on conventional two-dimensional ("2D") cell culture plastics tend to lose functional marker expression and failed to recapitulate their counterpart in vivo. Three-dimensional ("3D") culture proves to be powerful tool for recapitulate in vivo cell and tissue morphology and function. There is a need to make 3D cell culture systems accessible to biological laboratories. Current commercially available 3D culture systems are limited to scaffold-free 3D culture plates for aggregate formation in suspension, scaffold-based matrix discs for cell growth on the matrix, or in situ formation of alginate hydrogel beads. There is still an unmet need of 3D culture system that allows for easy manipulation, high density cell growth, sustained release of growth factor, co-culture with one or multi-types of cells. One or more embodiments of encapsulation of the present disclosure provides a solution to the aforementioned problems. In addition, in embodiments encapsulation of the present disclosure also provide a solution to tissue engineering and cell therapy product development.

In embodiments, the present disclosure includes the manipulation of process parameters to determine the output diameters of the one or more tubular structures, wherein the manipulated process parameters may include one or more of the following: (i) alginate concentration; (ii) alginate temperature; (iii) alginate sterilization method; (iv) inner diameter of the silica tip; and (v) inner diameter of a stainless-steel needle.

In embodiments, the diameter of micro-strands increases with an increase in the inner diameter ("ID") of a silica tip while decreasing with the increase of the concentration of alginate.

In embodiments, the present disclosure includes a method to produce one or more tubular structures and/or encapsulate objectives in such a tubular structure. The tubular structure may include one or more of the following: (a) strands, (b) tubes, (c) ribbons, and (d) fibers. The tubular structures may be: (a) nano-scale, (b) micro-scale, (c) macro-scale, and/or (d) up to meters in length.

In embodiments, the present disclosure includes one or more tubular structures with one or more encapsulated objectives, such as: (i) cells; (ii) tissues; (iii) organoids; (iv) microorganism; (iv) viruses (vi) macromolecules, such as: (a) proteins, (b) DNA, (c) RNA, (d) lipids, (e) polysaccharides; (vii) exosomes; (viii) biocatalysts; and (ix) pharmacological agents, such as: (a) drugs, (b) genes, and (c) vaccines.

Embodiments of the present disclosure may be used to form tubular structures with one or more of the following features, including: (i) scalable; (ii) handleable; (iii) cost-effective; and (iv) versatile encapsulation system.

Embodiments of the present disclosure may be used for one or more of the following applications, including: (i) 3D cell culture; (ii) drug delivery; (iii) gene delivery; (iv) vaccine; (v) cryopreservation; (vi) fermentation; and (vii) biocatalysts.

Embodiments of the present disclosure may include one or more of the following: (i) a two-syringe set up to form hydrogel tubular structures; (ii) a needle-in-needle device; (iii) the injection of cells into hydrogel microtubes; (iv) the use of microtubes for organoid formation, such as: (a) lentoid bodies, (b) retinoids, and (c) salivary gland organoids; (v) the configuration of a two-syringe device; (vi) the configuration of a two or three-way needle-in-needle device; (vii) the use of an aqueous alginate solution such as a 6% alginate solution; (viii) the use of tubes for cell culture that have a diameter in the range from 800 to 3,000 μm.

Embodiments of the present disclosure may include one or more of the following: (i) 3D cell culture; (ii) high density cell culture; (iii) stem cell expansion and differentiation; (iv) organoid culture; (v) tissue engineering; (vi) cell delivery and/or cell therapy; (vii) cell storage; (viii) tumor model;

(ix) drug testing; (x) 3D bioprinting; (xi) fermentation; (xii) enzyme immobilization; and (xiii) control release.

Embodiments of the present disclosure may involve or include one or more of the following: (i) alginate hydrogel microtubes; (ii) alginate hydrogel microtube kits for 3D cell culture; (iii) alginate hydrogel microtube kits for stem cells; (iv) microfluidic device and/or system for fabrication of microtubes with cells; (v) microfluidic device and/or system for fabrication of microtubes without cells; (vi) hydrogel microtube encapsulation kits; (vii) hydrogel microtube encapsulation system; and (viii) customized cell encapsulation in hydrogel microtubes.

Embodiments of the present disclosure may involve or include cell growth in hydrogel microtubes, wherein cells may include one or more of the following: (i) embryonic stem cells; (ii) mesenchymal stem cells; (iii) lens epithelial cell differentiation for lentoid formation; (iv) co-culture of salivary gland epithelial cells and fibroblasts; (v) salivary gland epithelial cells; and (vi) fibroblasts.

Embodiments of the present disclosure may include the use of a syringe-in-syringe and/or a needle-in-needle device to produce one or more hydrogel tubular structures. The syringe-in-syringe device may enable repeatable, manual formation of one or more tubular structures. The needle-in-needle device may enable repeatable, manual formation of one or more tubular structures.

Embodiments of the present disclosure involve or include the manipulation of process parameters to effect one or more microtube structure formation. The produced microtubes may include one or more of the following features: (i) high density cell growth; (ii) long-term cell growth; (iii) high density and long-term cell growth (e.g., mouse ESCs, lens epithelial cells, 3T3 fibroblasts, SIMS salivary gland epithelial cells); (iv) organoid formation (e.g., lentoid); and (v) co-culture of cells (e.g., 3T3 and SIMS cells).

Syringe-In-Syringe Apparatus Embodiment

Figure 1B:
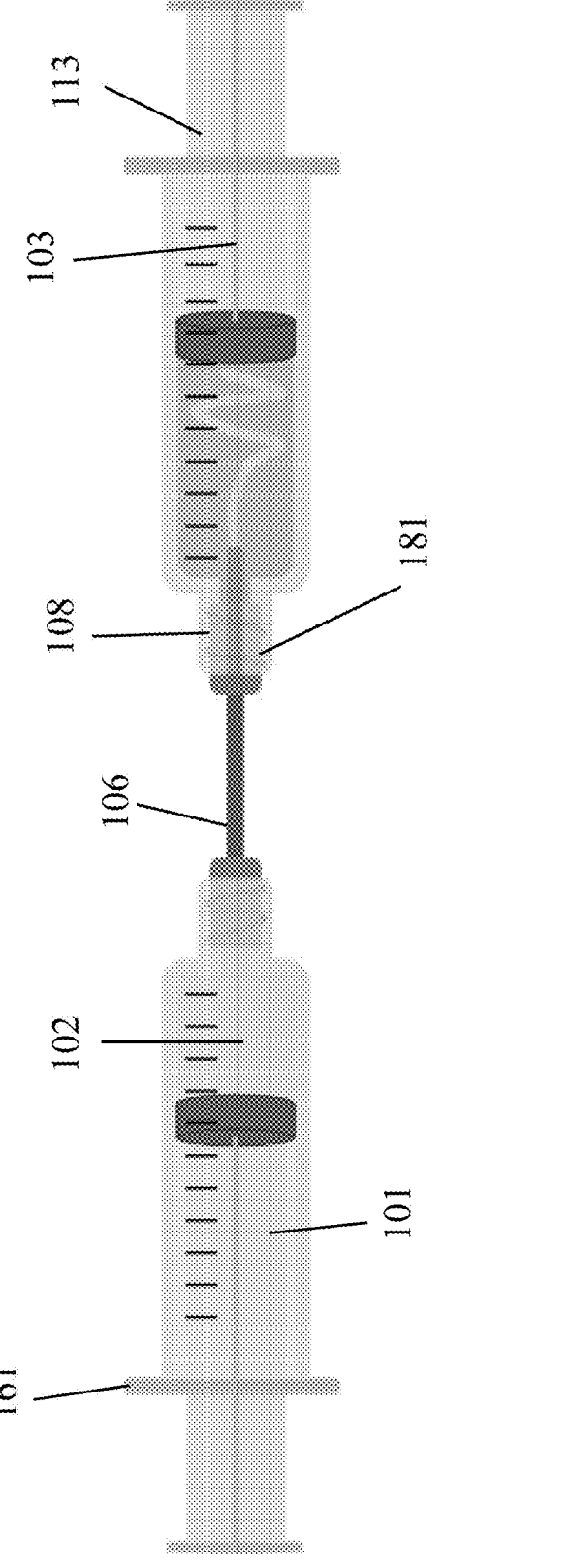

Referring not now to FIGS. 1A and 1B, a syringe-in-syringe apparatus or apparatus 100 of the present disclosure is shown including a first reservoir 101, and a second reservoir 103. In embodiments, the first reservoir 101 includes a solution of one or more hydrogel agents 102 of the present disclosure. In embodiments, the one or more hydrogel agents 102 of FIG. 1 is an alginate solution with an alginate concentration of 0.5 to 10% such as 3%, 4%, 5%, or 6%. In embodiments, the second reservoir 103 contains a solution of one or more cross-linking agents 104. In embodiments, cross-linking agents 104 is a cross-linking agent described above such as a solution of calcium chloride ($CaCl_2$)), or an aqueous solution of calcium chloride dihydrate.

In embodiments, the first reservoir 101 is connected to a first needle 106 that is an in-flow/out-flow point for the first reservoir 101. In embodiments, the second reservoir 103 is connected to the first needle or a second needle 110 that is an in-flow/out-flow point for the second reservoir 103. In embodiments, the first needle 106 is connected to an adapter 108. In embodiments, the second needle 110 is connected to adapter 108. In embodiments, the purpose of adapter 108 is to connect first needle 106 and/or second needle 110, specifically, to insert first needle 106 into the second reservoir, or second needle 110. In embodiments, the adapter 108 is made of a plastic, rubber, polymer, synthetic polymer, or foam material. In embodiments, first needle 106 has a smaller gauge (e.g., diameter) than second needle 110. In embodiments, first needle 106 and second needle 110 are fixed in place by the adapter 108, such that the first needle 106 and second needle 110 are in fluid communication. In embodiments, first needle 106 and second needle 110 are coupled together by the adapter 108, such that the first needle 106 and second needle 110 are in fluid communication, wherein liquid may pass from the first needle 106 to the second needle 110, and vice versa, without liquid leaking into the surrounding environment. In embodiments, the adapter has a preselect size configured to join the first needle 106 and second needle 110 such that fluid may pass between the first needle 106 and second needle 110 without leakage. As shown in FIG. 1B, only the first needle 106 connects the first reservoir 101 and second reservoir 103. Here, the first needle 106 passes through the adapter and into fluid communication with the second reservoir 103. In embodiments such as those in FIG. 1B, the adapter is positioned within a distal opening 181 of a second syringe. In embodiments, the adapter 108 closes off distal opening 181 to prevent leakage of fluids within the device such as fluid from second reservoir.

In embodiments, plunger 113 of the second reservoir 103 is withdrawn in a pull motion 114. The pull motion 114—on plunger 113—creates a vacuum that enables the one or more hydrogel agents 102 to be pulled into the one or more cross-linking agents 104. In embodiments, the vacuum created is in the amount of 250 to 650 Torr at room temperature or 4 to 37 degrees C. In embodiments, the pull motion 114 may be generated by hand force or that or a machine.

In embodiments, the first reservoir 101, and the second reservoir 103 are sized according to the amount of fluid anticipated to be within the first reservoir 101, and the second reservoir 103. Non-limiting examples of suitable sizes for the first reservoir 101, and the second reservoir 103 include 5 ml, 10 ml, 20 ml, or larger. In embodiments, methods include drawing one or more hydrogel agents 112 into one or more cross-linking agents 104, wherein hydrogel agents 112 is the same solution as hydrogel agents 102 (e.g., an alginate solution with an alginate concentration of 6%) described above.

Alternatively, in embodiments, one or more hydrogel agents 102 of FIG. 1 may be an aqueous alginate solution with an alginate concentration of 1-20%, 1-15%, 1-10%, about 10%, about 9%, about 8%, about 7%, about 6%, about 5%, about 4%, about 3%, about 2%, or 5%, 4%, 3%, or 2%.

In embodiments, the one or more hydrogel agents 102 of FIG. 1 may be a solution that includes alginate and one or more of the following materials, including: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; and (xvii) vaccines. For example, hydrogel agents 102 may be a solution that contains alginate of 6% concentration and epithelial lens cells. Alternatively, hydrogel agents 102 may be a solution that contains alginate of 6% concentration and any types of cells, such as embryonic stem cells (ESCs).

In embodiments, one or more crosslinking agents 104 of FIG. 1 may include a $CaCl_2$) solution that contains $CaCl_2$) and polylysine. In embodiments, the $CaCl_2$) is an aqueous solution.

In embodiments, the first needle 106 and second needle 110 have gauges that are equal in size. For example, first needle 106 has a gauge that is equivalent to the gauge of second needle 110. In embodiments, the first needle 106 and second needle 110 may each be characterized as having a gauge between 10 gauge and 34 gauge, such as e.g., 10-gauge, 15-gauge, 20-gauge, 25 gauge, or 30 gauge. In embodiments, gauge refers to the inner measurement or opening of the needle.

In embodiments, FIG. 1 depicts an apparatus 100 for forming one or more microfibers or other 3D structures of the present disclosure, including a conduit 170 for flowing a hydrogel agent through conduit 170 from a first reservoir 101 to a second reservoir 103 including a crosslinking agent under conditions suitable for forming one or more microfibers within the second reservoir 103, wherein flowing includes pulling the hydrogel agent into the second reservoir 103 through the conduit 170, and wherein the conduit 170 includes a first needle 106 and second needle 110 attached by an adapter 108, wherein the first needle 106 and second needle 110 are in fluid communication. In embodiments, adapter 108 is disposed over and atop the first needle 106 and the second needle 110. In embodiments, pulling includes moving a plunger 113 disposed within a syringe 171 away from the adapter 108 under conditions sufficient to form a vacuum. In embodiments, a first reservoir 101 is disposed within a first syringe 161 and the second reservoir 103 is disposed within a second syringe 171.

Figure 2:
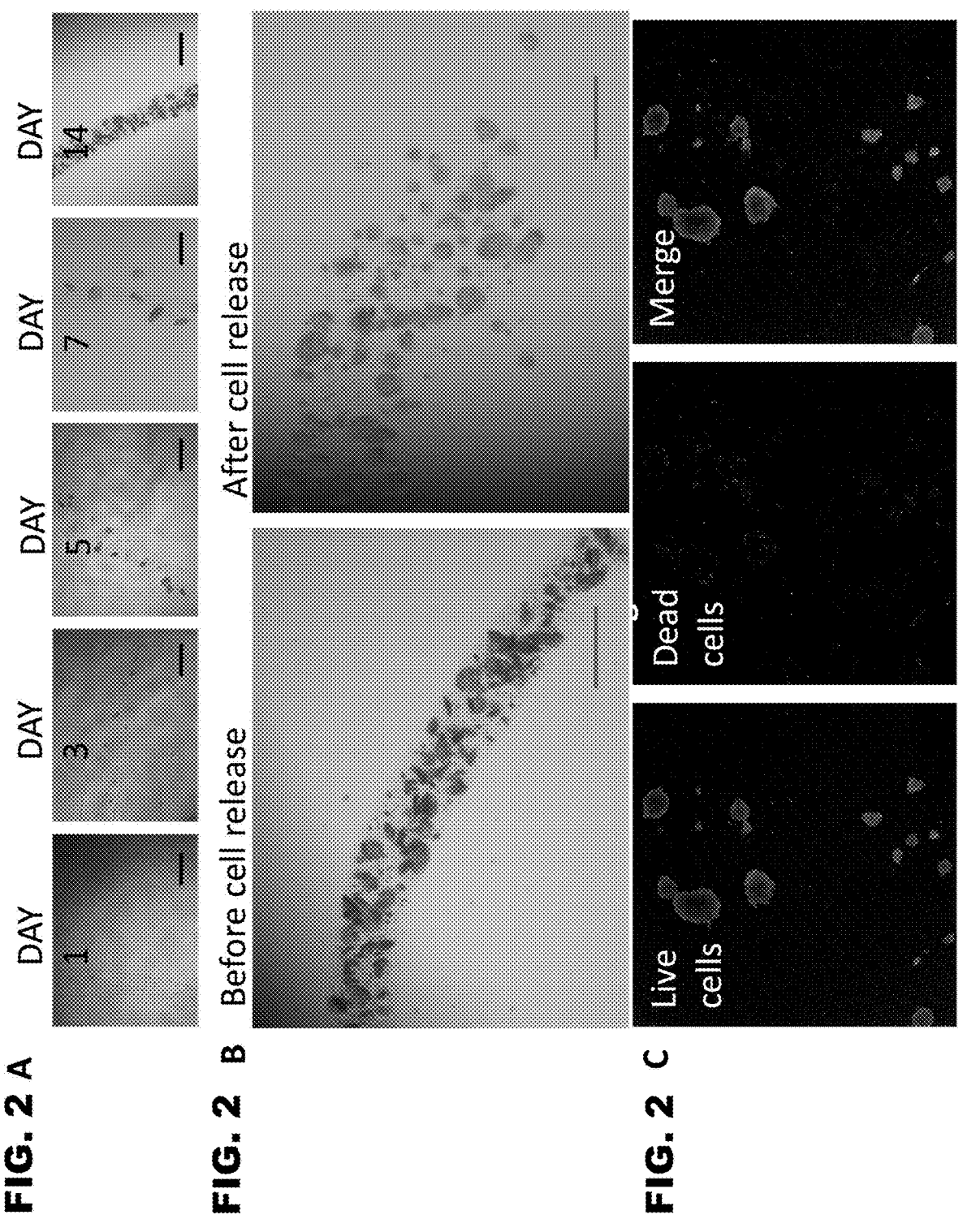
FIGS. 2A-2C depict alginate hydrogel microfibers or micro-strands, made of 6% alginate, that facilitate high density cell culture using ESCs.

Referring now to FIG. 2A. FIG. 2A depicts alginate hydrogel microfibers or micro-strands, made of 6% alginate, that facilitate high density cell culture using ESCs for 14 days. FIG. 2B depicts cell release from hydrogel by incubating with sodium citrate solution. FIG. 2C depicts retention of high viability in cell aggregates while only individual cells are dead and revealed by live/dead staining.

Syringe-In-Syringe Filter Apparatus Embodiment

Figure 3:
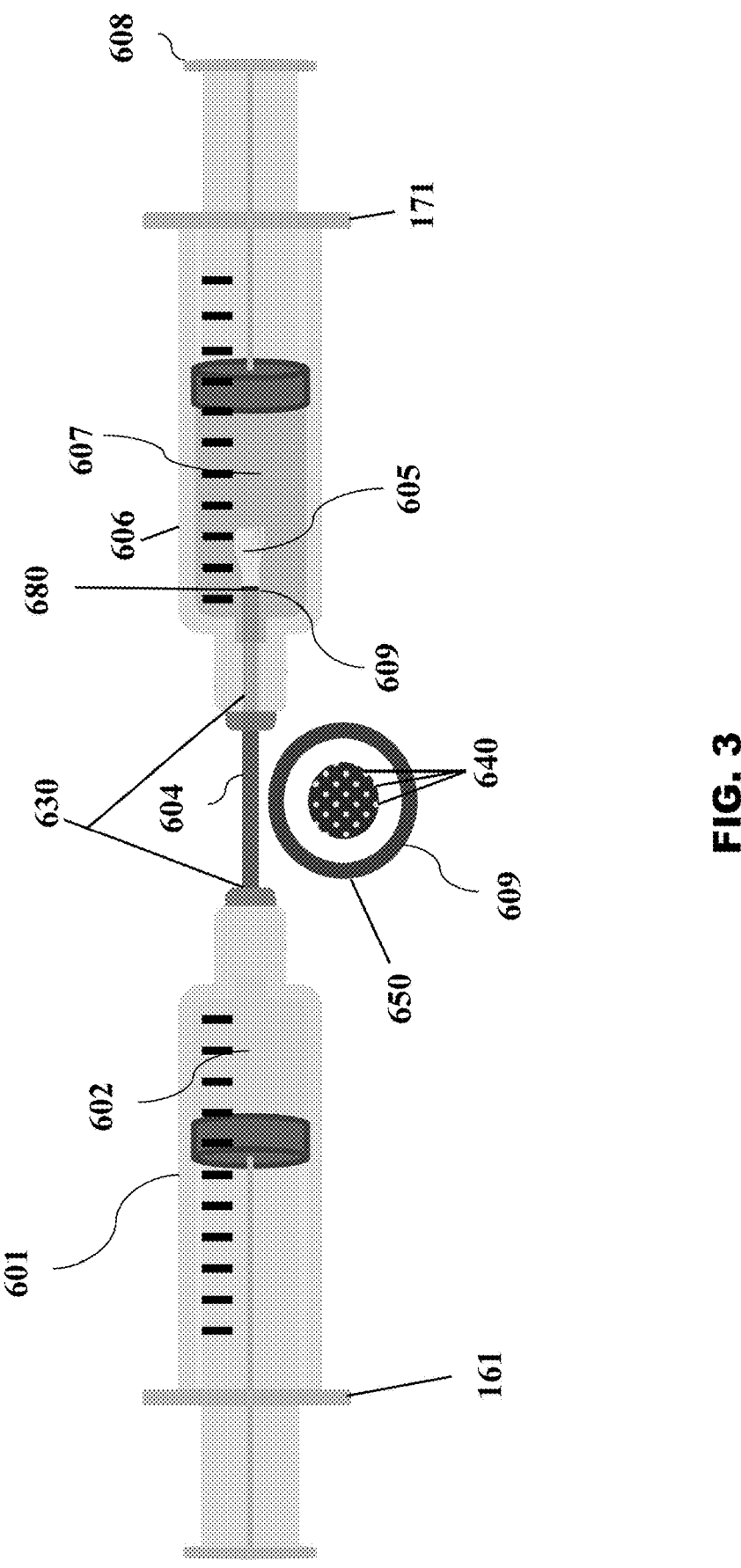
FIG. 3 is a diagram of a needle-in-needle apparatus containing a filter insert with an array of pores in accordance with the present disclosure.

FIG. 3 represents one or more embodiments of the present disclosure characterized as a syringe-in-syringe apparatus with a filter. In embodiments, the apparatus contains a first syringe 161, a second syringe 171, and a filter 609. The first syringe includes a first reservoir 601 that includes a hydrogel agent 602 or the present disclosure. In embodiments, hydrogel agent 602 is an alginate solution. In embodiments, the second syringe includes a second reservoir 606 that contains a crosslinking agent 607 or the present disclosure, such as a CaCl₂ solution.

In embodiments, the first syringe and second syringe are connected via an adapter 604. In embodiments, the first syringe and second syringe are connected via an adapter 604 and form a conduit 630. In embodiments, a primary purpose of the connection is to draw the contents of the first reservoir 601 (i.e., hydrogel agent 602) into the second reservoir 606 (i.e., crosslinking agent 607). Rather than create a single strand, the embodiment depicted in FIG. 3 includes a filter 603 that draws an array of micro-strands 605 into the second reservoir 606. In embodiments, filter 609 in an opening 680 of the conduit 630 within the second reservoir, wherein the filter 609 a plurality of holes 640.

The filter 609 is placed at the end of the first syringe and separates the hydrogel agent into an array of micro-strands 605 that are pulled into the second reservoir by pulling the plunger 608 of the second syringe 171. The location of filter 603 is shown in FIG. 3 as filter 609 at the end of the first syringe. In the present embodiment, the alginate solution (i.e., hydrogel agent 602) of the first reservoir 601 of the first syringe is drawn into the CaCl₂ solution (i.e., cross-linking agent 607) of the second reservoir 606 of the second syringe when the plunger 608 of the second syringe is pulled. The filter 603, such as a micropatterned SU-8 filter, creates an array of micro-strands 605 of the alginate solution (i.e., hydrogel agent 602) that are then embedded within the CaCl₂ solution (i.e., cross-linking agent 607) of the second reservoir 606. In embodiments, the micropattern of the filter includes a plurality of spaced holes. As hydrogel agent 602 is pulled through the plurality of holes 640 disposed in filter 609 (a front filter view 650 is also provided in FIG. 3), a plurality of micro-strands or an array of micro-strands are formed within second reservoir 606 as the hydrogel agent contacts the cross-linking agent 607 under conditions suitable for cross-linking the hydrogel agent to form a cross-linked hydrogel.

In embodiments, an array of micro-strands 605 are removed from the second reservoir 606 after the process has finished and the device is disassembled. Alternatively, the array of micro-strands 605 may be directly injected into the human body. For example, the array of micro-strands 605 may be used for a surgical procedure that requires an array of micro-strands to be inserted into the tissue of a medical patient. Rather than remove the micro-strands from the second reservoir 606, the array of micro-strands 605 may be injected directly into the desired location.

Figure 4:
FIG. 4 depicts bundles of alginate hydrogel fibers formed by the syringe-in-syringe apparatus of the present disclosure with a micropatterned SU-8 filter.

FIG. 4 depicts bundles of alginate hydrogel fibers formed by the syringe-in-syringe apparatus with a micropatterned SU-8 filter. FIG. 4 is a byproduct produced from one or more embodiments that incorporate a micropatterned filter as exemplified by FIG. 3. The byproduct of FIG. 4 is not the exclusive product of the syringe-in-syringe apparatus and is not meant to be the limited use/product of the syringe-in-syringe apparatus.

Syringe-In-Syringe with Needle-In-Needle Apparatus

Figure 5A:
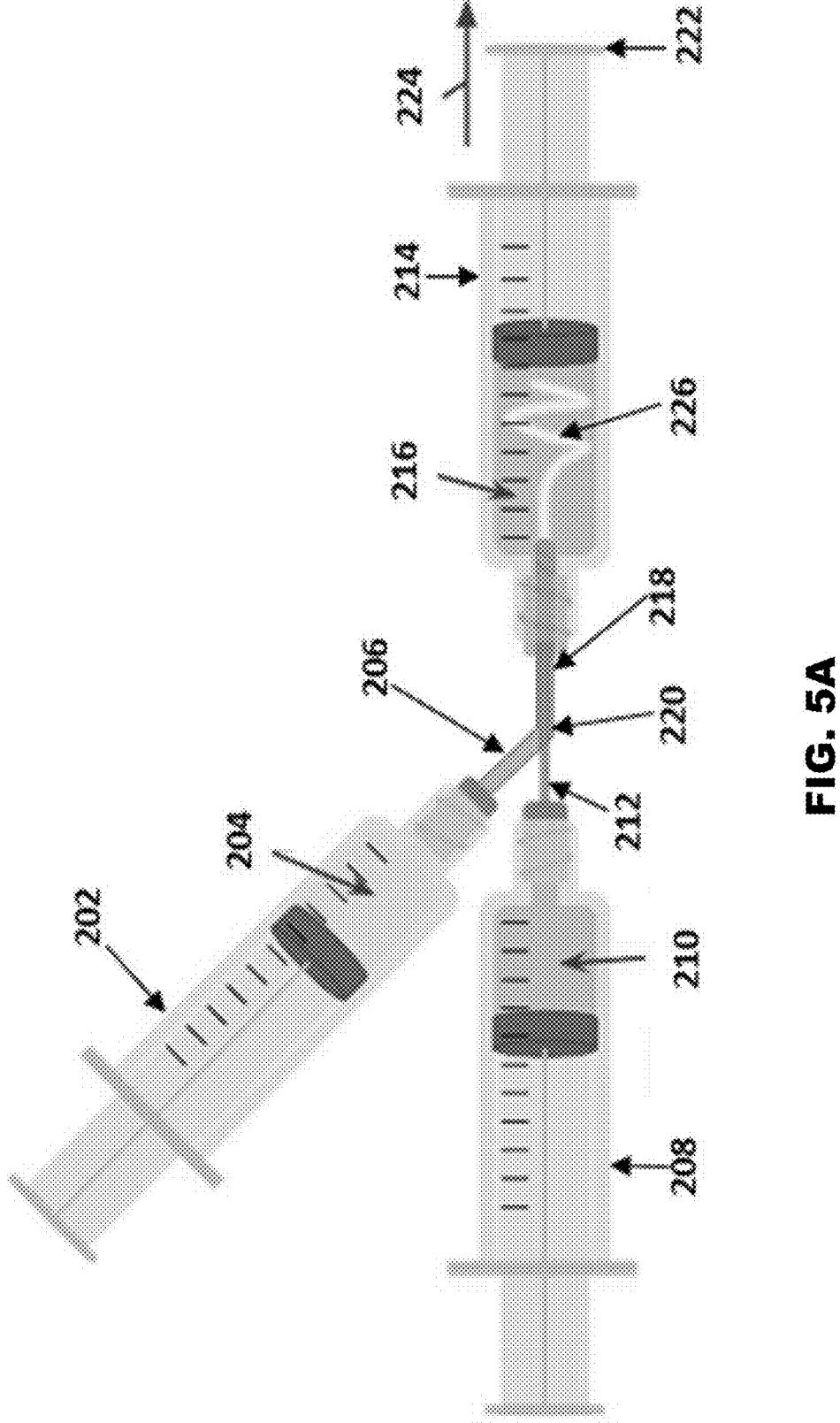
FIGS. 5A-5F depict a syringe-in-syringe apparatus with needle-in-needle apparatus (FIGS. 5A and 5D) in accordance with the present disclosure.
Figures 5B, 5C:
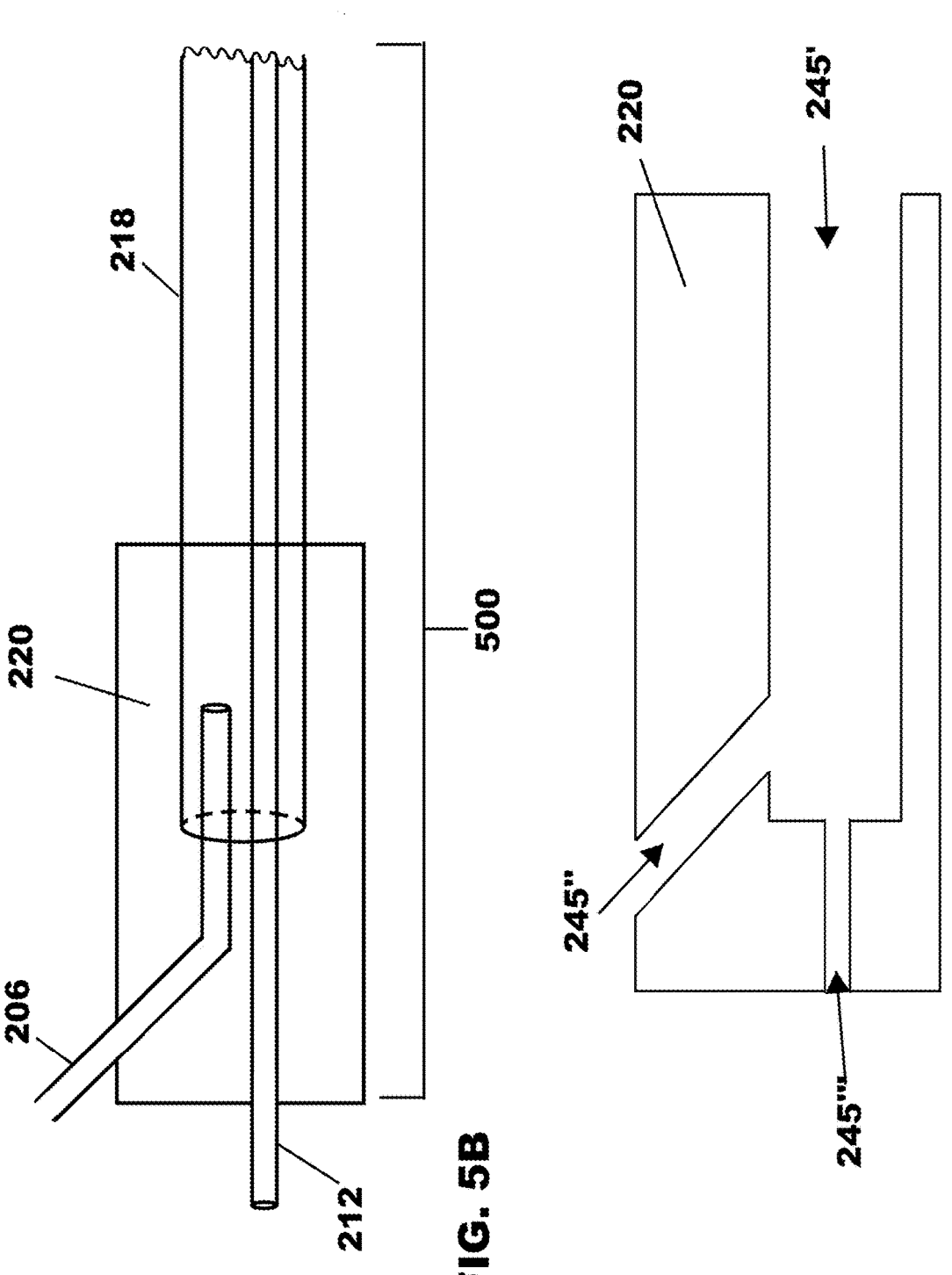
Figure 5D:
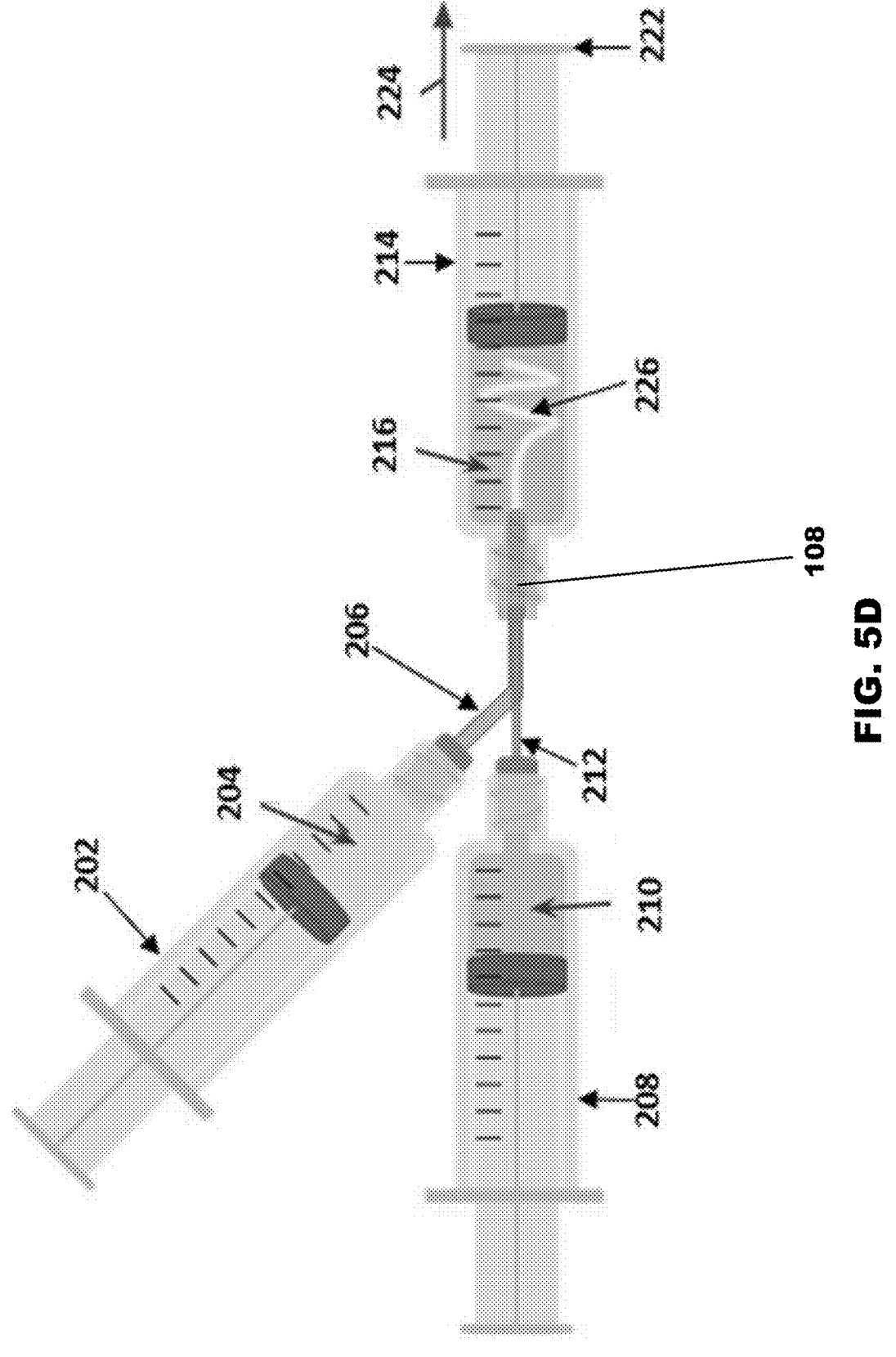
Figure 5E:
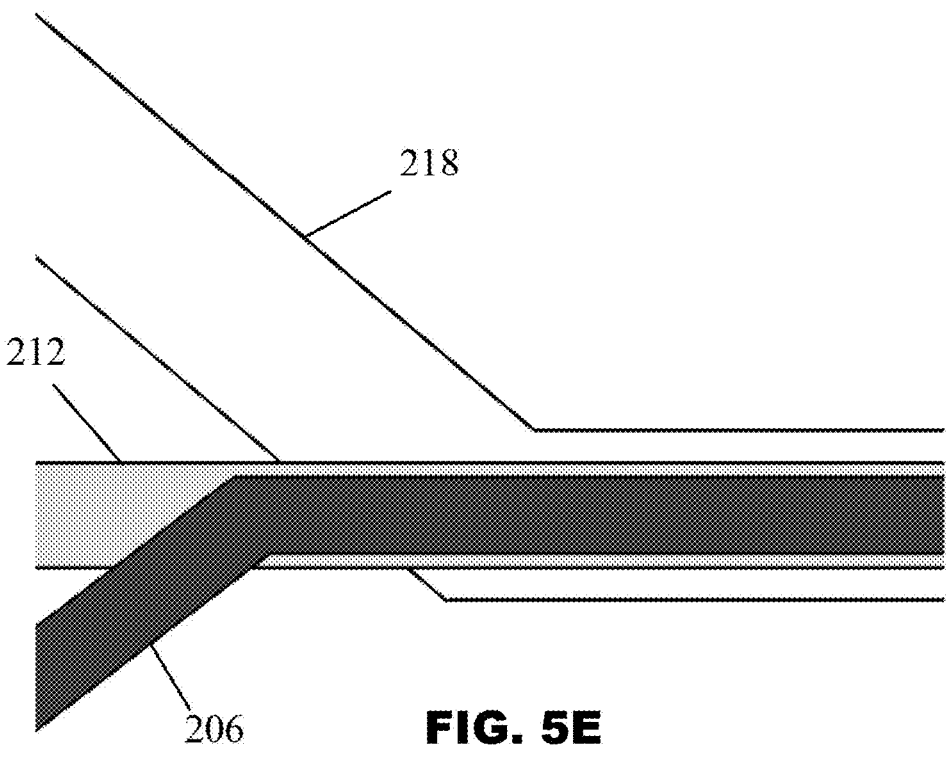
Figure 5F:
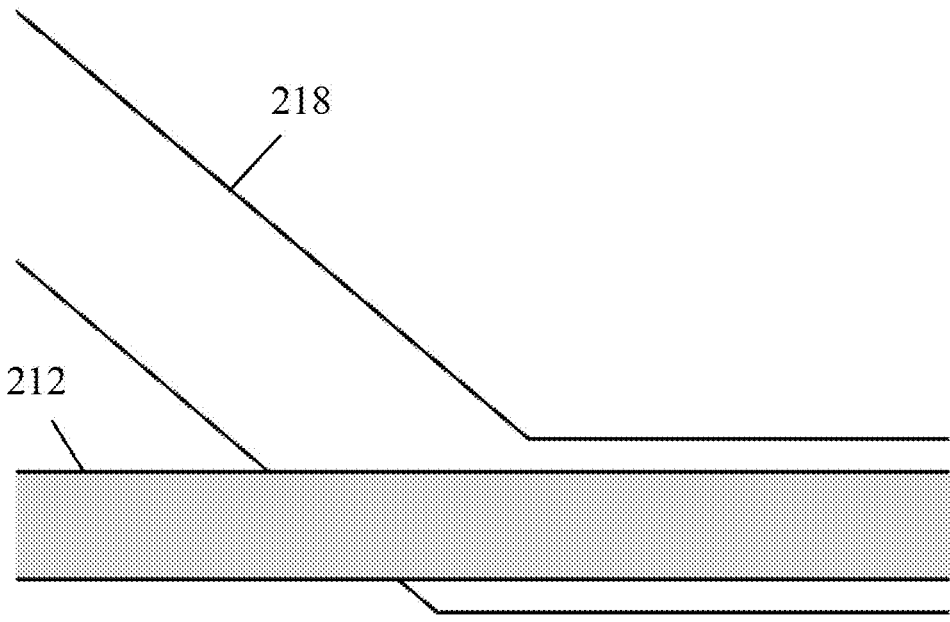

FIG. 5A-5F depict a syringe-in-syringe apparatus with needle-in-needle apparatus (FIGS. 5A and 5D) in accordance with the present disclosure. FIG. 5B is a cross-sectional side view of a conduit 500 in accordance with the present disclosure with an adapter 508. FIG. 5C is a cross-section side view of an adapter 508 embodiment of the present disclosure. FIGS. 5E and 5F are cross-sectional side views of a conduits in accordance with the present disclosure, such as needle-in-needle conduits. FIG. 5A represents one or more embodiments of the present disclosure which contain a syringe-in-syringe with needle-in-needle apparatus. In the present embodiment, FIGS. 5A and 5D contains a first reservoir 202, a second reservoir 208, and a third reservoir 214.

In embodiments, the first reservoir 202 includes a hydrogel agent 204. In the present embodiment, hydrogel agent 204 is an alginate solution. In embodiments, the second reservoir 208 includes a crosslinking agent 210. In embodiments, crosslinking agent 210 is a CaCl₂) solution. In embodiments, the third reservoir 214 includes a crosslinking agent 216. In the present embodiment, crosslinking agent 216 is a CaCl₂) solution.

In embodiments, the first reservoir 202 is a syringe, part of which is a needle 206. The second reservoir 208 is a syringe, part of which is a needle 212. The third reservoir 214 is a syringe, part of which is a needle 218. As shown in FIG. 5B, in embodiments, needle 206, needle 212, and needle 218, are all connected to an adapter 220. In embodiments, needle 206, needle 212, and needle 218, are in fluid communication and connected to the adapter 220. In embodiments, the adapter 220 has three inputs (245', 245", and 245''')—one for each needle (i.e., needle 206, needle 212, needle 218; collectively, "The Needles")—that enable The Needles to be connected despite differences in diameter.

In embodiments, needle 218 has the largest diameter (e.g., gauge) with respect to needle 206 and needle 212. Accordingly, input 245' may also have the largest diameter with respect to input 245" and input 245'. The connection of The Needles of all syringes is to facilitate a vacuum sealed transfer of material between reservoirs. Specifically, hydrogel agent 204 within first reservoir 202 and crosslinking agent 210 within second reservoir 208 will be transferred—in whole or in part—to the third reservoir 214. In embodiments, the transfer will occur via a pulling motion 224 on plunger 222 that is connected to the third reservoir 214. The pulling motion 224 will create a vacuum that draws hydrogel agent 204 and crosslinking agent 210 into the third reservoir 214. As a result, a user determined amount of hydrogel agent 204 and crosslinking agent 216 will become embedded within crosslinking agent 216, as exemplified by hydrogel agent/crosslinking agent 226.

Alternatively, one or more embodiments may include a hydrogel agent other than an alginate solution. As a further alternative embodiment, one or more embodiments may include a cross-linking agent other than a CaCl$_2$) solution. As yet a further alternative embodiment, one or more organic materials may be mixed with the hydrogel agent employed. As yet a further alternative embodiment, one or more organic materials may be mixed with the cross-linking agent employed.

Alternatively, one or more embodiments, may include a conduit including a second needle within a first needle. For example, referring to FIG. 5, second needle 212 enters into an opening in the side of needle 206 and extends until contacting the second reservoir. In embodiments, first needle 206 includes the second needle within a central or substantially central location with the interior portion, and first needle 206 extends until contacting the second reservoir. In embodiments, first needle 206 and second needle 212 may pass through adapter 108 positioned within a distal opening of the second syringe.

Syringe-In-Syringe with Three Needle-In-Needle Apparatus

Figure 6A:
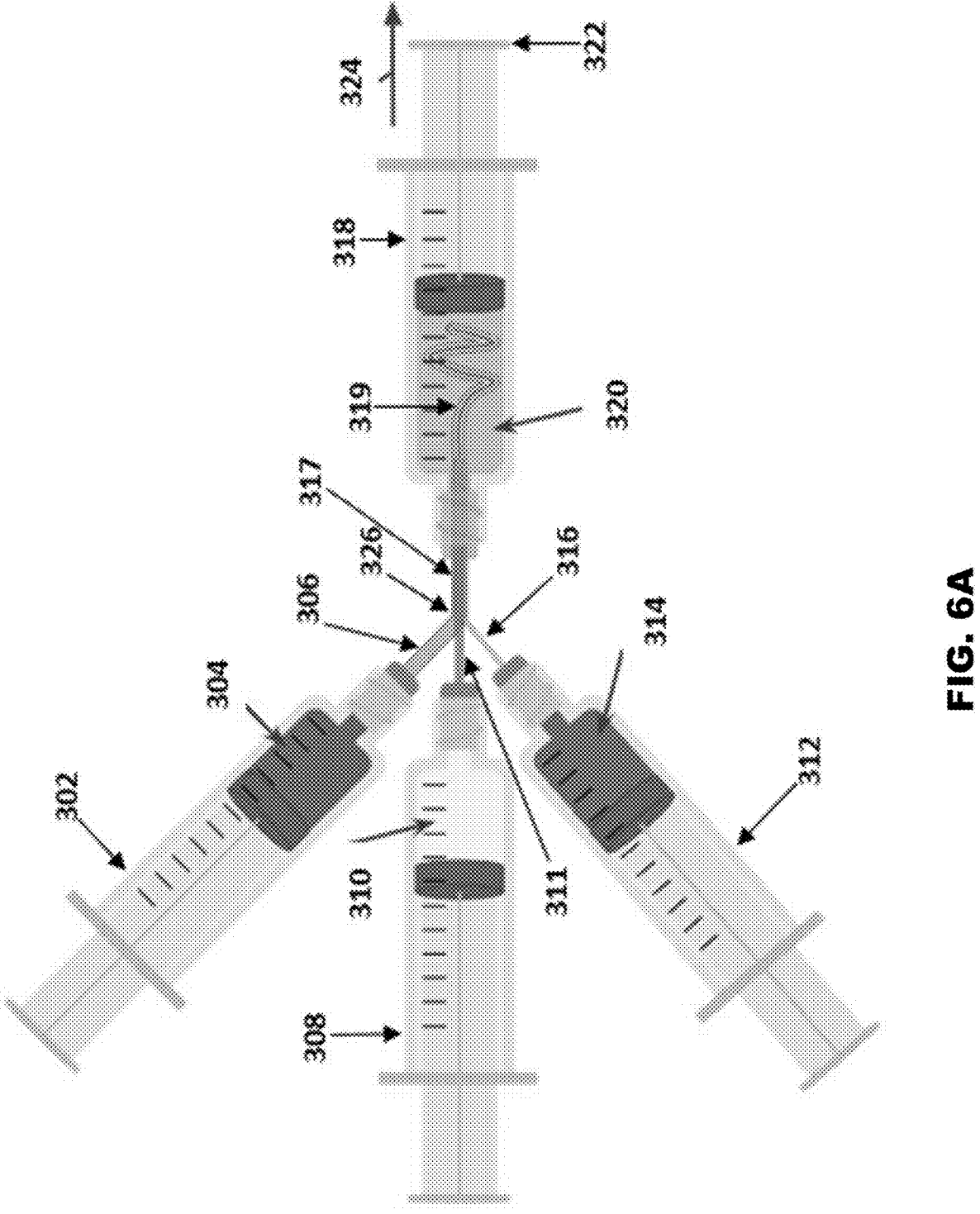
FIG. 6A-6C depict a syringe-in-syringe apparatus with a three needle-in-needle apparatus in accordance with the present disclosure.
Figure 6B:
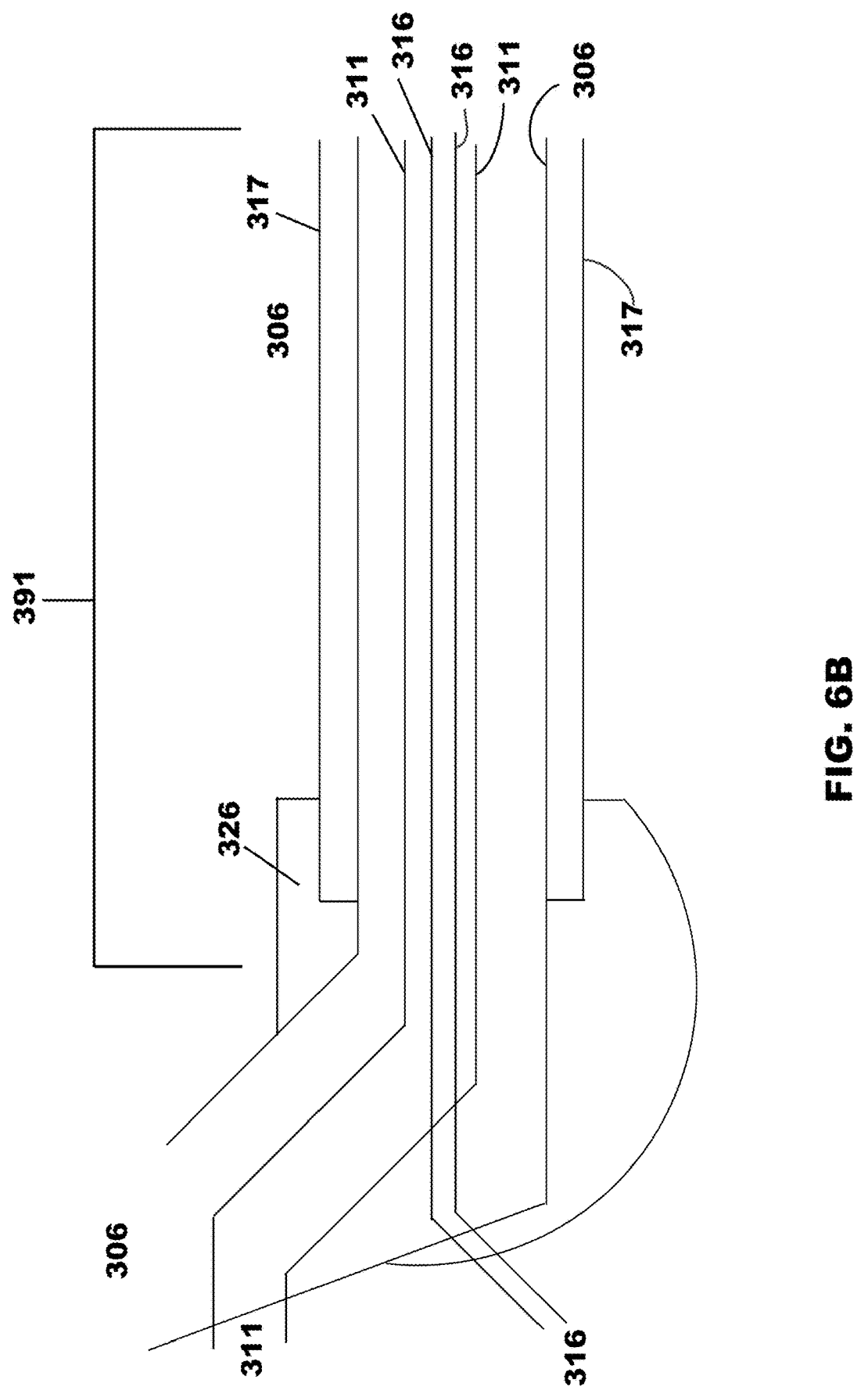
Figure 6C:
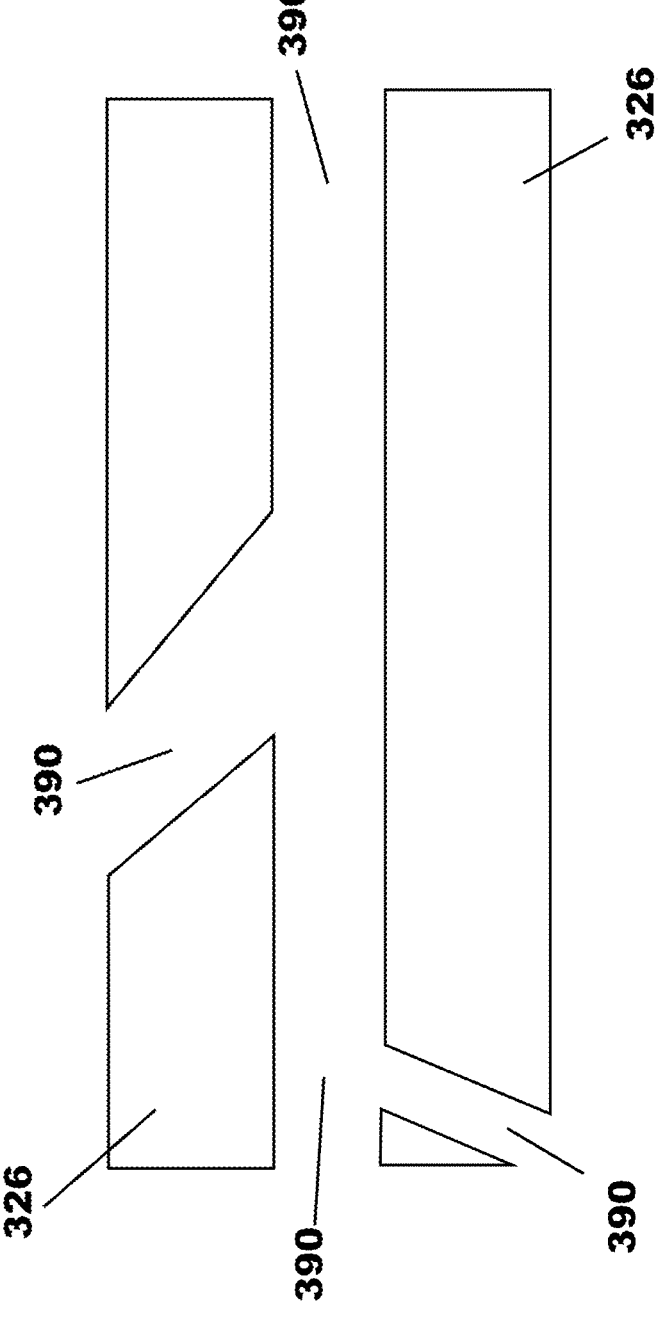

FIG. 6 represents one or more embodiments of the present invention which include a syringe-in-syringe with three needle-in-needle apparatus. In embodiments, FIG. 6 contains a first reservoir 302, a second reservoir 308, a third reservoir 312, and a fourth reservoir 318 (collectively, "The Reservoirs 302/308/312/318"). In embodiments, the first reservoir 302, a second reservoir 308, a third reservoir 312, and a fourth reservoir 318 are all in fluid communication.

In embodiments, the first reservoir 302 is a syringe that contains a crosslinking agent 304 and is connected to a needle 306. In embodiments, crosslinking agent 304 is a CaCl$_2$), or CaCL$_2$ solution that contains polylysine, and/or chitosan, micro-molecule cross-linker. In embodiments, the second reservoir 308 is a syringe that contains a hydrogel agent 310 and is connected to a needle 311. In embodiments, hydrogel agent 310 is an alginate solution wherein the alginate concentration is 6%. In embodiments, the third reservoir 312 is a syringe that contains a crosslinking agent 314 and is connected to a needle 316. In embodiments, crosslinking agent 314 is a CaCl$_2$) solution. In embodiments, the fourth reservoir 318 is a syringe that contains a crosslinking agent 320 and is connected to a needle 317. In the present embodiment, crosslinking agent 320 is a CaCl$_2$) solution.

In embodiments, the Reservoirs 302/308/312/318 are connected via an adapter 326. The adapter 326 has at least four inputs, one input 390 for each needle that is connected to Reservoirs 302/308/312/318 (e.g., one input 390 each for the following: needle 306, needle 311, needle 316, and needle 317). Adapter 326 permits the connection of needles of various gauges to be securely connect to each other to enable transfer of materials contained within one or more of the reservoirs to be transferred to one or more of another reservoirs. Referring to FIG. 6B, an embodiment shows the interconnection between needle 306, needle 311, needle 316, and needle 317. In embodiments, needle 316 passes through needle 306, and needle 311 to be centrally positioned within the conduit 391 and within needle 317. Further, needle 311 is shown passing through needle 306 to be centrally positioned within the conduit 391 and within needle 317. Further, needle 306 is shown centrally positioned within the conduit 391 and within needle 317. Adapter 326 is also shown surrounding the needles to prevent leakage therefrom.

In embodiments, crosslinking agent 304, hydrogel agent 310, and crosslinking agent 314, will be transferred, in whole or in part, to the fourth reservoir 318.

The transfer of the materials (e.g., crosslinking agent 304, hydrogel agent 310, and crosslinking agent 314) to the fourth reservoir 318 is done via a pulling motion 324 exerted on plunger 322 that is connected to the fourth reservoir 318. The pulling motion 324 creates a vacuum that draws crosslinking agent 304, hydrogel agent 310, and crosslinking agent 314 into the fourth reservoir 318, and thus into crosslinking agent 320.

The flow rate of materials from the first reservoir 302, second reservoir 308, and third reservoir 312, may be controlled via adapter 326 to ensure that the input material 319 is transferred in appropriate ratios and proper conformation.

Alternatively, one or more embodiments may include a hydrogel agent other than an alginate solution. As a further alternative embodiment, one or more embodiments may include a cross-linking agent other than a CaCl$_2$) solution. As yet a further alternative embodiment, one or more organic materials may be mixed with the hydrogel agent employed. As yet a further alternative embodiment, one or more organic materials may be mixed with the cross-linking agent employed.

Syringe-In-Container Apparatus

Figure 7:
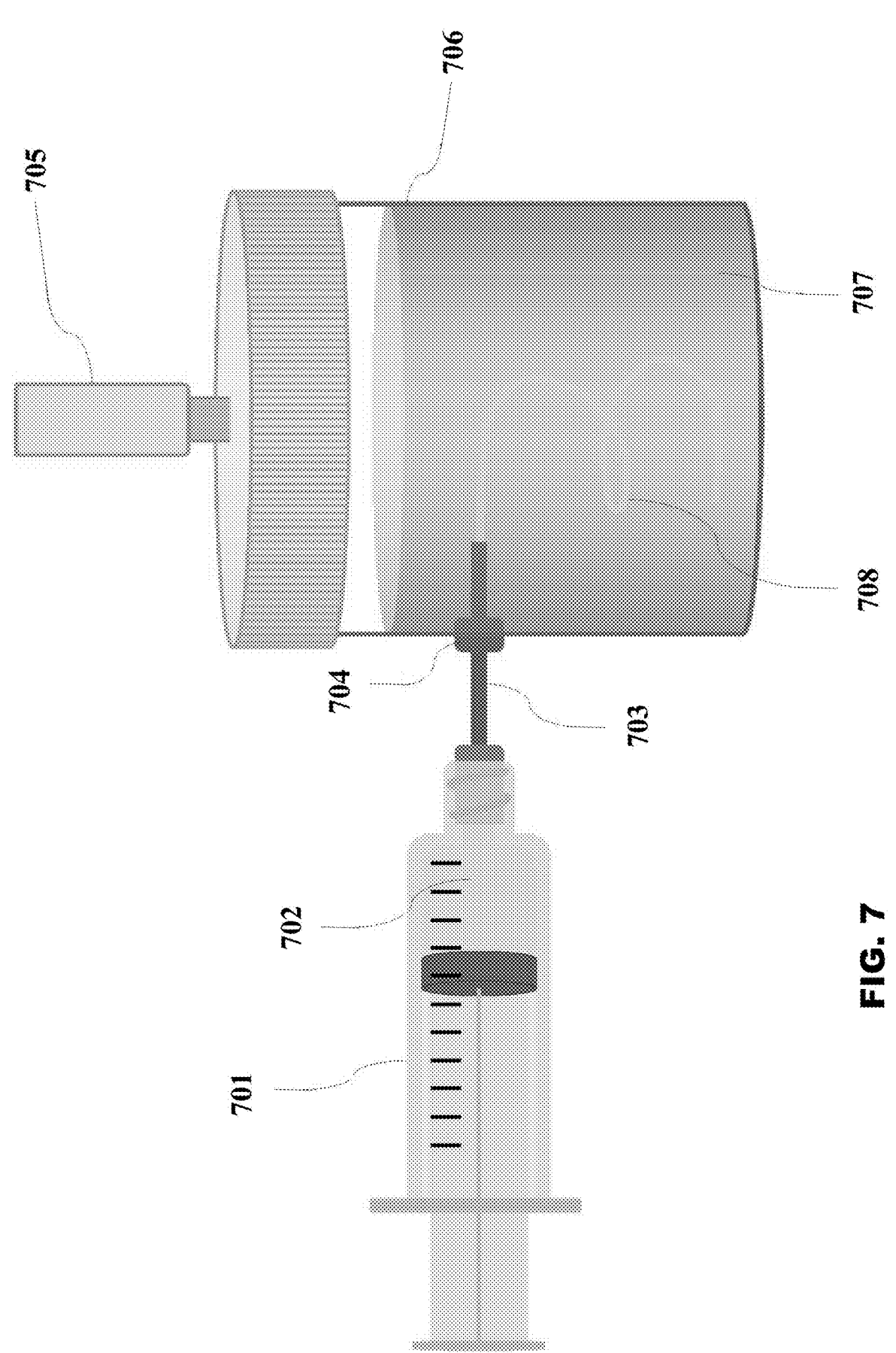
FIG. 7 is a diagram of a syringe-in-container apparatus in accordance with the present disclosure.

FIG. 7 depicts a syringe-in-container apparatus of the present disclosure. In embodiments, a syringe is horizontally connected to a container and a vacuum pump is vertically connected to a container. In embodiments, the syringe contains a first reservoir 701. The first reservoir 701 of the syringe contains a hydrogel agent 702; in the present embodiment, hydrogel agent 702 within the first reservoir 701 of the syringe is an alginate solution.

The syringe needle 703 is connected to the container 706 via an adapter 704. The adapter 704 creates an air-tight seal between the syringe and the container 706 to maintain pressure and/or prevent leakage of solution within the container.

The container 706 contains a cross-linking agent 707; in embodiments, cross-linking agent 707 is an aqueous solution of CaCl$_2$). In embodiments, a vacuum pump 705 is connected vertically (with respect to the orientation of the container 706) to the top of the container 706. The vacuum pump 705 is operated at a user determined pressure. The vacuum pump 705 may be operated manually by the user or controlled by one or more computer programs.

The vacuum pump 705 draws the content from the first reservoir 701 of the syringe into the container 706. In the present embodiment, vacuum pump 705 draws an alginate solution micro-strand 708 into the solution of cross-linking agent 707 within container 706. The micro-strand 708 is drawn into container 706 and collects on the bottom of container 706.

Figure 8:
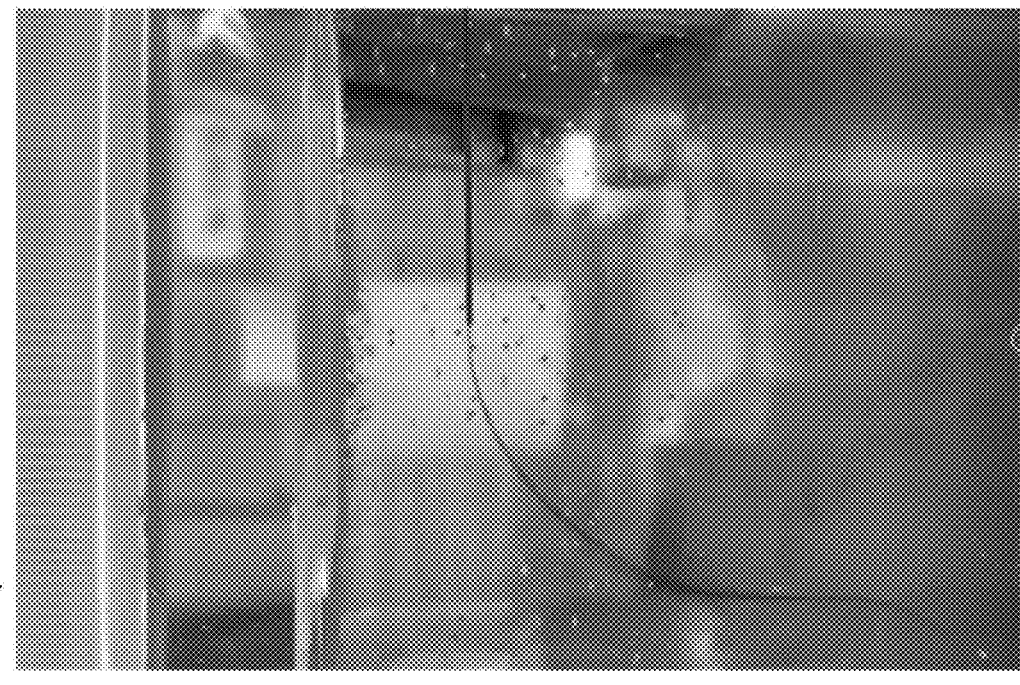
FIG. 8 depicts the process of producing a long microfiber or micro-strand using the syringe-in-container apparatus of the present disclosure.
Figure 8:
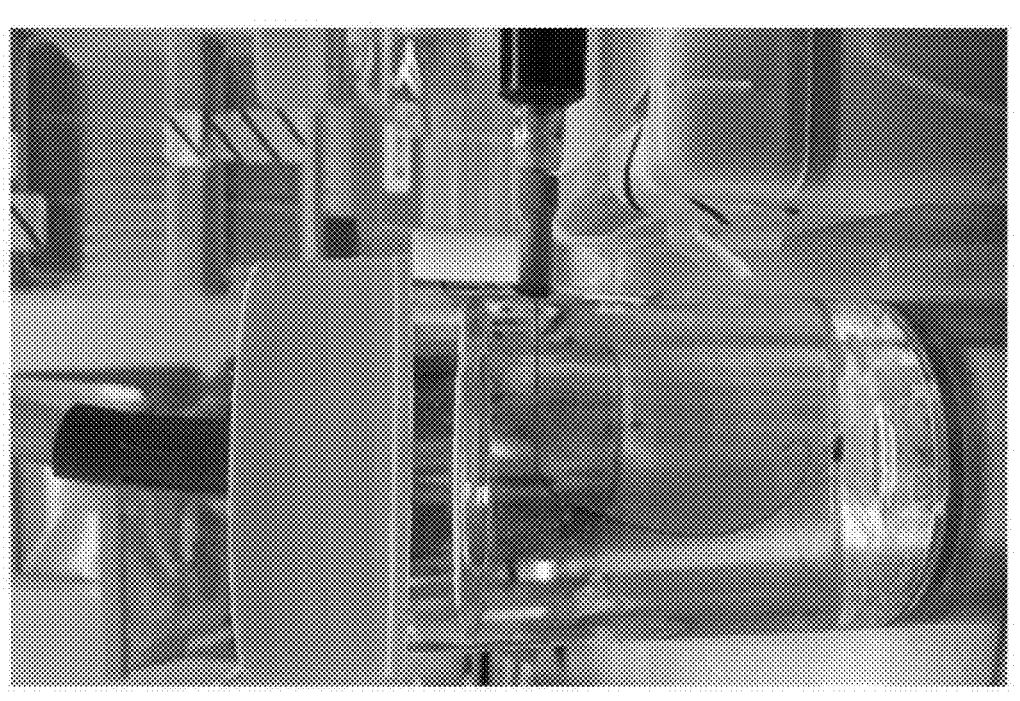

FIGS. 8A-8C depict an embodiment of a process of producing a long microfiber or micro-strand using the syringe-in-container apparatus of the present disclosure. FIGS. 8A-8C show a timeline of the syringe-in-container apparatus being used in a laboratory environment. FIGS. 8A-8C shows a vacuum pump drawing the contents of a syringe into the solution of a container at three intervals of time. FIG. 8A represents a first point in time. FIG. 8B represents a second point in time. FIG. 8C represents a third and final point in time.

Figure 9:
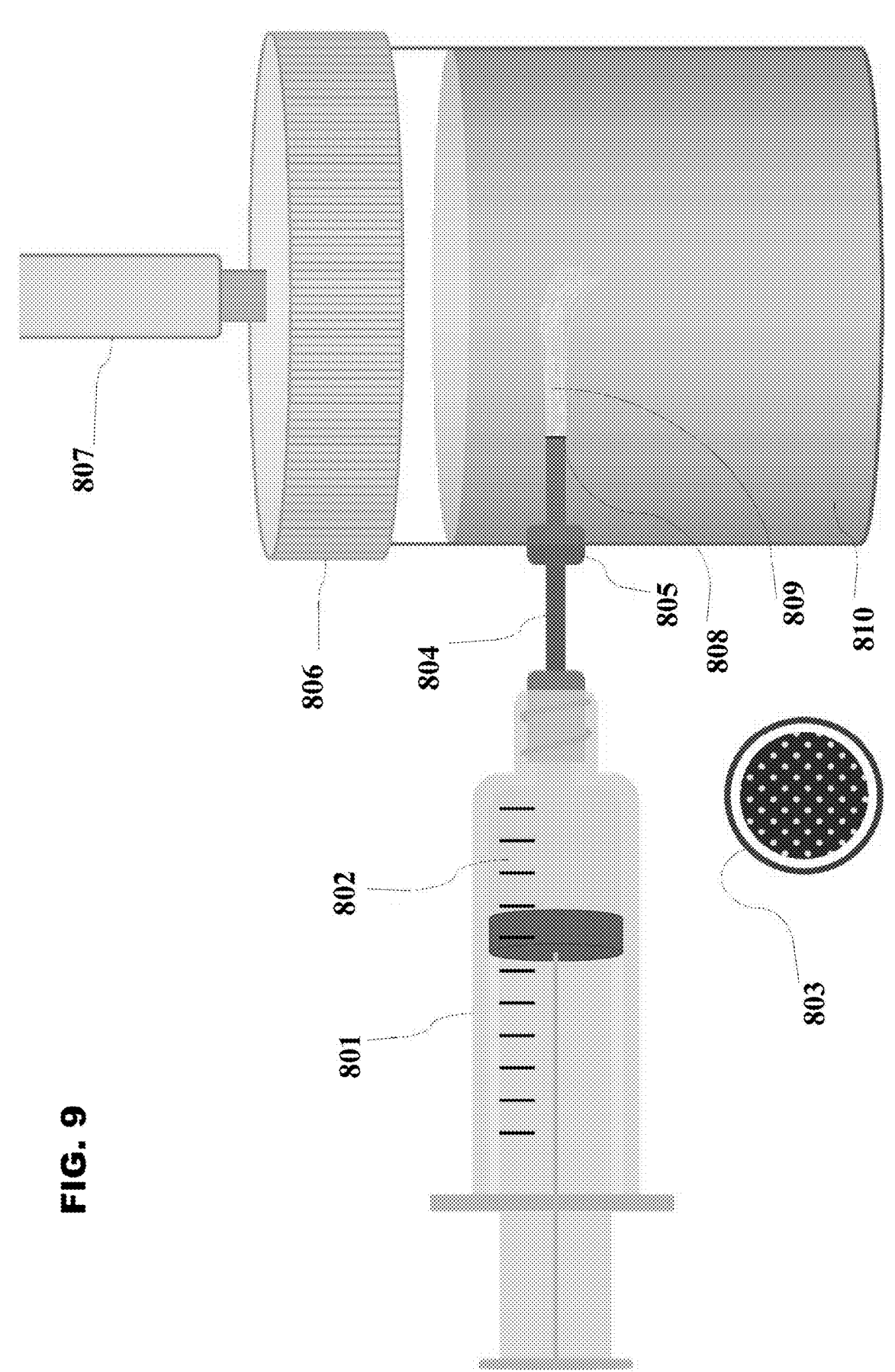
FIG. 9 is a diagram of a syringe-in-container apparatus of the present disclosure with a filter insert with an array of pores.

FIG. 9 depicts a syringe-in-container apparatus with a filter insert with an array of pores. In the present embodiment, a syringe is horizontally connected to a container and a vacuum pump is vertically connected to the container.

The syringe contains a first reservoir 801. The first reservoir 801 of the syringe contains a hydrogel agent 802; in the present embodiment, hydrogel agent 802 within the first reservoir 801 of the syringe is an alginate solution.

In the present embodiment, the syringe needle 804 is connected to a container 806 via an adapter 805. Adapter 805 creates an air-tight seal between the syringe and container 806 to maintain pressure within the system.

The end of the syringe is connected to a filter 808 insert with an array of pores as shown by the cross-sectional view of the filter 803. In the present embodiment, the filter 808 insert is a SU-8 filter.

Alternatively, a filter insert of different dimensions may be used to produce an array of micro-strands wherein the micro-strands may be comprised of one or more dimensions.

The container 806 contains a cross-linking agent 810; in the present embodiment, cross-linking agent 810 is an aqueous solution of $CaCl_2$).

Alternatively, the container may contain any cross-linking agent that is compatible with the one or more hydrogel agents being drawn into the container. As a further embodiment, the aqueous solution within the container may contain a solution of $CaCl_2$) and one or more compatible substances. A vacuum pump 807 is connected vertically (with respect to the orientation of the container 806) to the top of the container 806. Vacuum pump 807 is operated at a user determined pressure. In the present embodiment, vacuum pump 807 is manually controlled. Alternatively, vacuum pump 807 may be controlled by one or more computer systems and software programs.

Vacuum pump 807 draws the content from first reservoir 801 of the syringe into container 806. In the present embodiment, vacuum pump 807 draws an alginate solution array of micro-strands 809 into the aqueous solution of $CaCl_2$) within container 806. The SU-8 filter 808 creates the array of micro-strands 809 of alginate solution. The array of micro-strands 809 is drawn into the container 806 and collect on the bottom of container 806.

Alternatively, one or more embodiments may include a hydrogel agent other than an alginate solution. As a further alternative embodiment, one or more embodiments may include a cross-linking agent other than a $CaCl_2$) solution. As yet a further alternative embodiment, one or more organic materials may be mixed with the hydrogel agent employed. As yet a further alternative embodiment, one or more organic materials may be mixed with the cross-linking agent employed.

Figure 10:
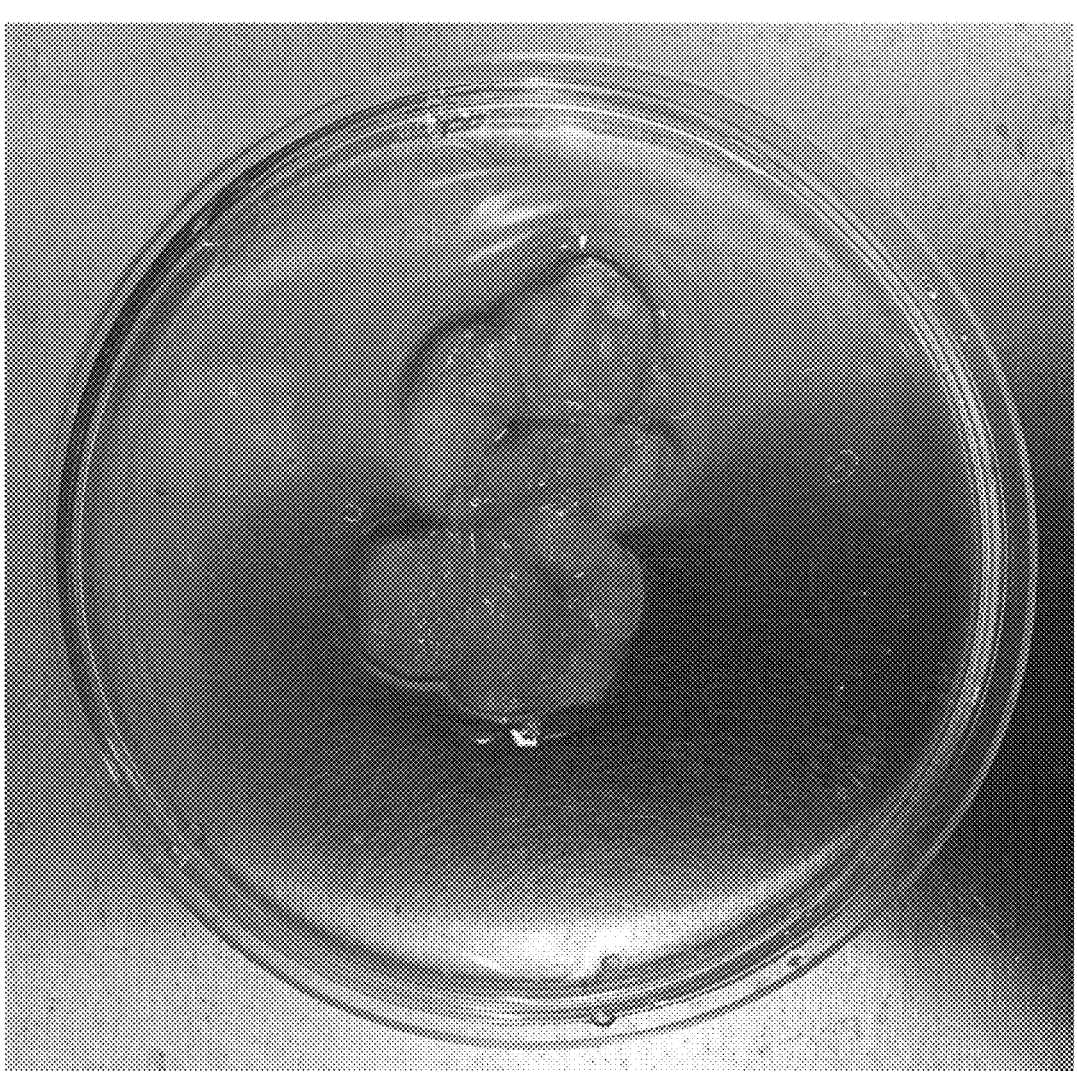
FIG. 10 depicts alginate hydrogel fibers formed by the syringe-in-syringe apparatus of the present disclosure with a micropatterned SU-8 filter.

FIG. 10 depicts alginate hydrogel fibers formed by the syringe-in-syringe apparatus with a micropatterned SU-8 filter. One or more embodiments, such as the syringe-in-container apparatus with a filter insert depicted in FIG. 9, may result in a product of alginate hydrogel fibers as depicted in FIG. 10.

Syringe-In-Container Apparatus with Needle-In-Needle Apparatus

Figure 11:
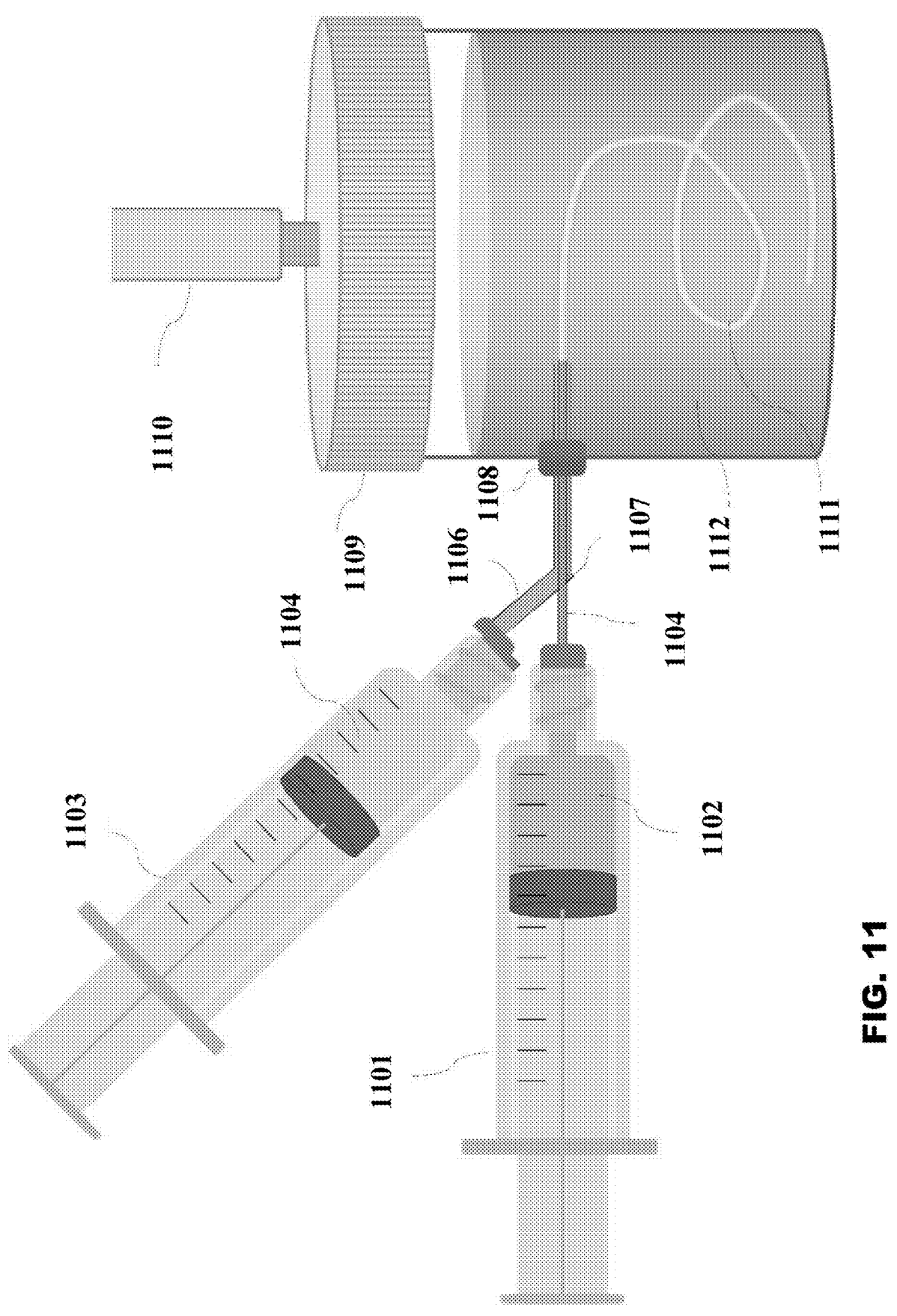
FIG. 11 is a diagram of a syringe-in-container apparatus with needle-in-needle apparatus of the present disclosure.

FIG. 11 depicts a syringe-in-container apparatus with needle-in-needle apparatus to form microtubes. In the present embodiment, FIG. 11 includes a first syringe, a second syringe, a container, a first adapter, a second adapter, and a vacuum pump.

The first syringe consists of a first reservoir 1101 and a first needle 1104. The first reservoir 1101 contains a cross-linking agent 1102. In the present embodiment, crosslinking agent 1102 is a solution of $CaCl_2$).

The second syringe includes a second reservoir 1103 and a second needle 1106. The second reservoir contains a hydrogel agent 1104. In the present embodiment, hydrogel agent 1104 is an alginate solution.

The first needle 1104 and the second needle 1106 are connected via a first adapter 1107. The connection enables the contents of the first reservoir 1101 and the second reservoir 1103 to be drawn into the container 1109 simultaneously.

The connected needles, are connected to the container 1109 via a second adapter 1108. The second adapter 1108 creates a vacuum seal so that the needles (e.g., first needle 1104 and second needle 1106) can be inserted into the container 1109 without a loss in pressure.

The vacuum pump 1110 is connected vertically to the container 1109 with respect to the orientation of the container 1109.

The vacuum pump 1110 creates pressure within the container 1109 that draws the contents of the first reservoir 1101 and the second reservoir 1103 into the aqueous solution of the container 1109. The contents of the first reservoir 1101 and second reservoir 1103 are drawn into the container 1109 in the form of a micro-strand 1111. The micro-strand 1111 is collected on the bottom of container 1109.

Alternatively, an array of micro-strands may be drawn into the container by using a filter insert. For example, a SU-8 filter may be at the end of the needle that is within the container and create a porous array of micro-strands as the contents of the first and second reservoir are drawn into the container from the pressure created by the vacuum pump.

Alternatively, one or more embodiments may include a hydrogel agent other than an alginate solution. As a further alternative embodiment, one or more embodiments may include a cross-linking agent other than a $CaCl_2$) solution. As yet a further alternative embodiment, one or more organic materials may be mixed with the hydrogel agent employed. As yet a further alternative embodiment, one or more organic materials may be mixed with the cross-linking agent employed.

Figure 12:
FIG. 12 is a diagram of symmetric and asymmetric microtubes of the present disclosure.

FIG. 12 represents two features that may be present in one or more embodiments of the present invention.

FIG. 12A is a diagram of symmetric microtubes, wherein the microtube strand of materials is symmetrical in shape with respect to the outer layer of material.

FIG. 12B is a diagram of asymmetric microtubes, wherein the microtube strand of materials an asymmetrical in shape with respect to the outer layer of material.

Figure 13:
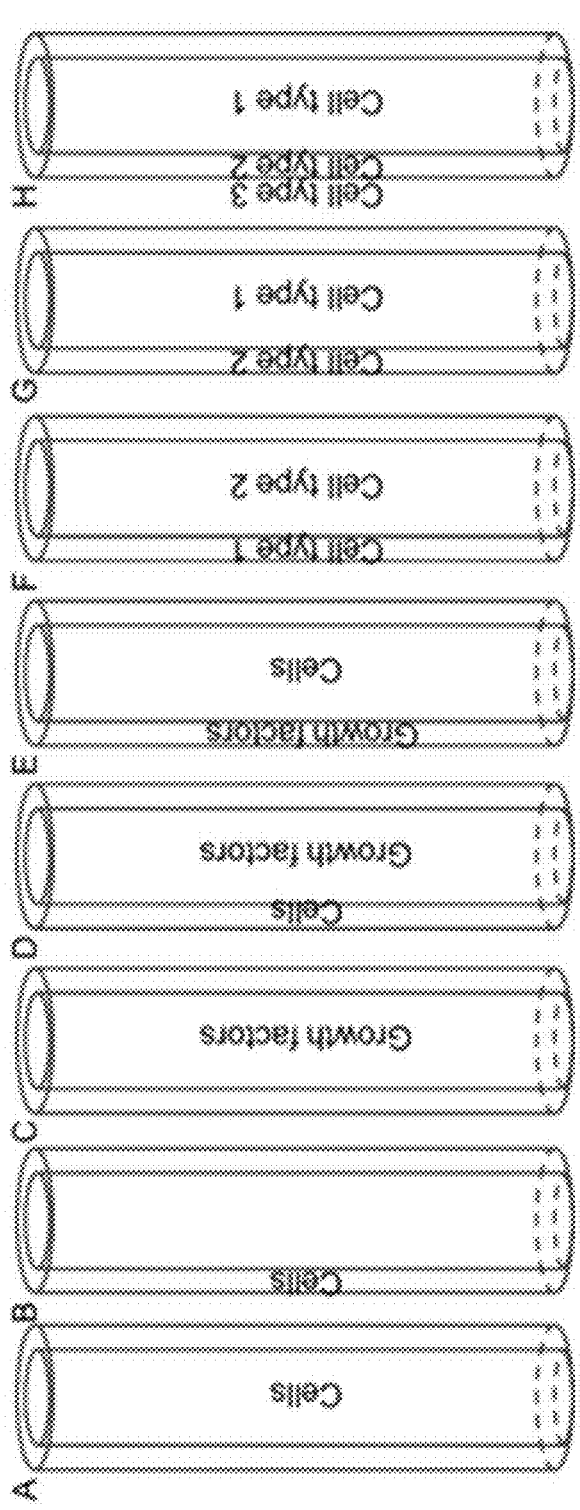
FIG. 13 is a diagram showing various configurations of microtubes of the present disclosure.

FIG. 13 is a diagram showing various configurations of microtubes. The diagrams of FIG. 5 represent a cylindrical product (i.e., microtube) that contains an inner layer and an outer layer.

FIG. 13A has a configuration wherein the inner layer includes cells.

FIG. 13B depicts a configuration wherein the outer layer includes cells.

FIG. 13C depicts a configuration wherein the inner layer includes growth factors.

FIG. 13D depicts a configuration wherein the inner layer includes growth factors and the outer layer includes cells.

FIG. 13E depicts a configuration wherein the outer layer includes growth factors and the inner layer includes cells.

FIG. 13F depicts a configuration wherein the outer layer includes a first cell type and the inner layer includes a second cell type.

FIG. 13G depicts the inverse of FIG. 13F wherein the outer layer includes a second cell type and the inner layer includes a first cell type.

FIG. 13H depicts a configuration wherein there are three layers, an inner layer includes a first cell type, a middle layer includes a second cell type, and an outside layer includes a third cell type.

Figure 14:
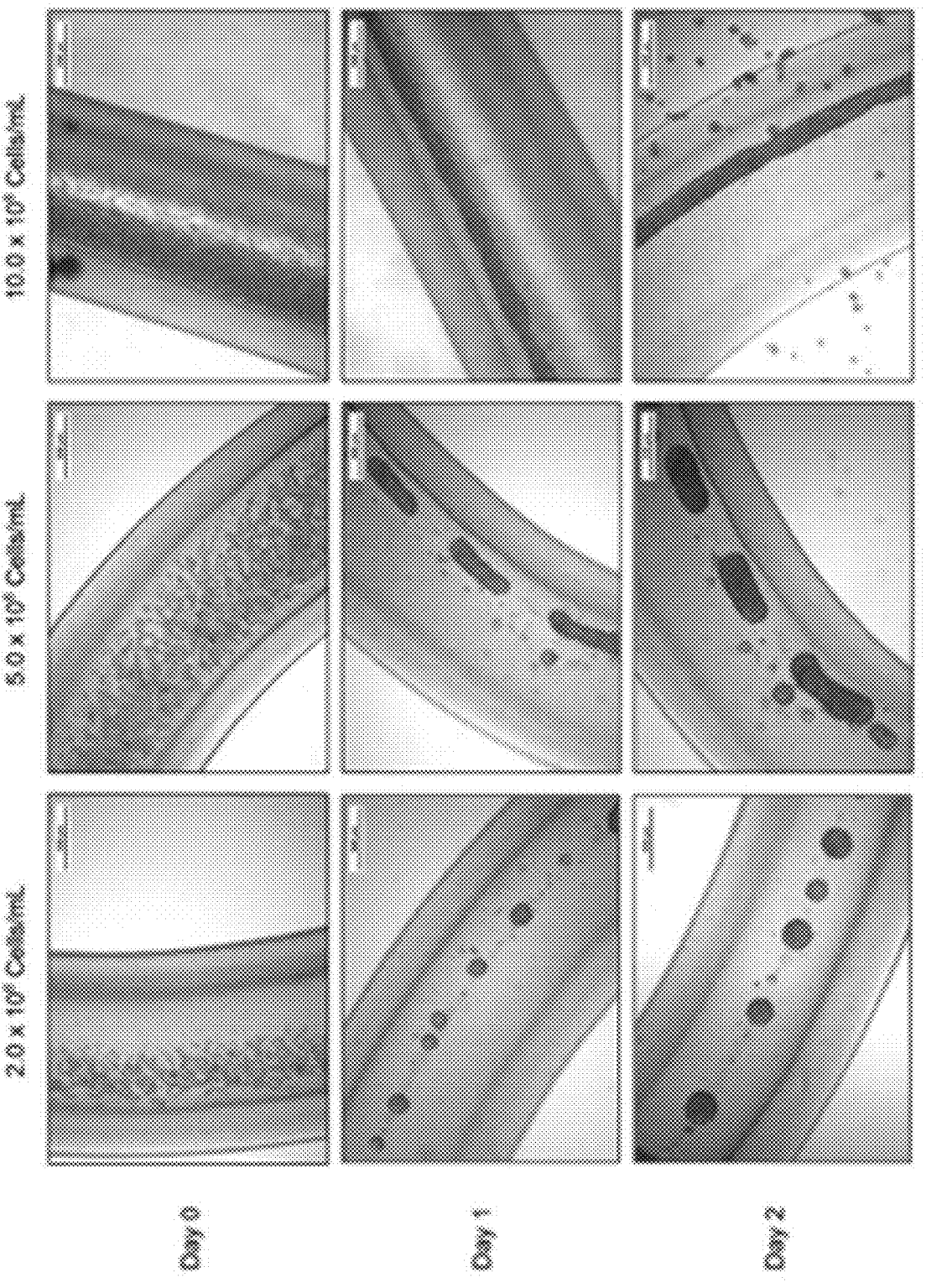
FIG. 14 depicts alginate hydrogel microtubes of the present disclosure, made of 6% alginate, that facilitate high density cell culture using ESCs.

FIG. 14 depicts alginate hydrogel microtubes made of 6% alginate to facilitate high density cell culture of ESCs. FIG. 14 shows snapshots—over a three-day period—of three alginate hydrogel microtubes with different concentrations of ESCs per milliliter. The concentration of cells within the alginate hydrogel microtubes are the following: (a) $2.0 \times 10^6$ cells/ml; (b) $5.0 \times 10^6$ cells/ml; and (c) $10.0 \times 10^6$ cells/ml.

Figure 15:
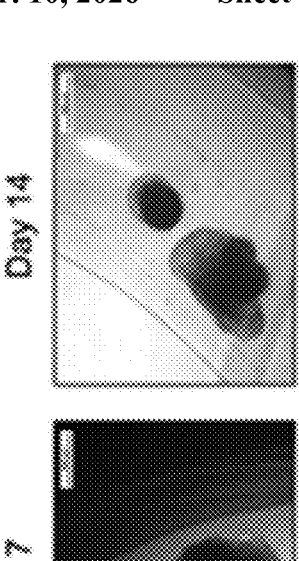
FIG. 15 is a timeline of alginate hydrogel microtubes of the present disclosure made of 3% alginate that allow long-term culture of embryoid bodies, a step for in vivo-like stem cell differentiation or organoid formation.
Figure 15:
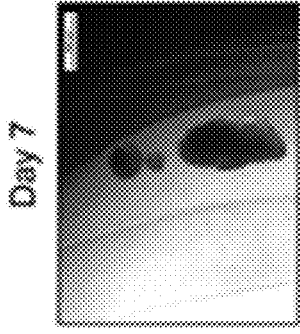
Figure 15:
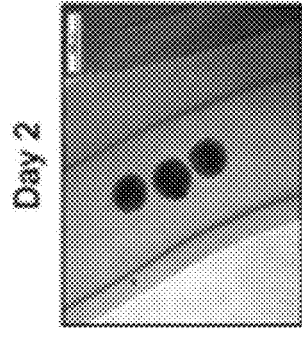
Figure 15:
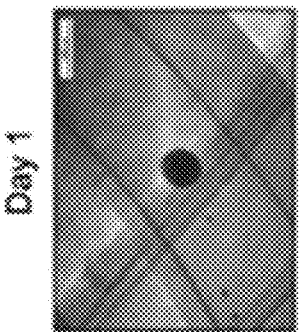
Figure 15:
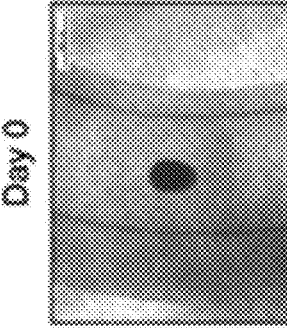

FIG. 15 depicts alginate hydrogel microtubes made of 3% alginate that enable long-term culture of embryoid bodies. FIG. 15 depicts the alginate hydrogel microtubes over a time period of fourteen-days with snapshots shown at Day 0, Day 1, Day 2, Day 7 and Day 14. This represents a critical step for in vivo-like stem cell differentiation and/or organoid formation.

Figure 16:
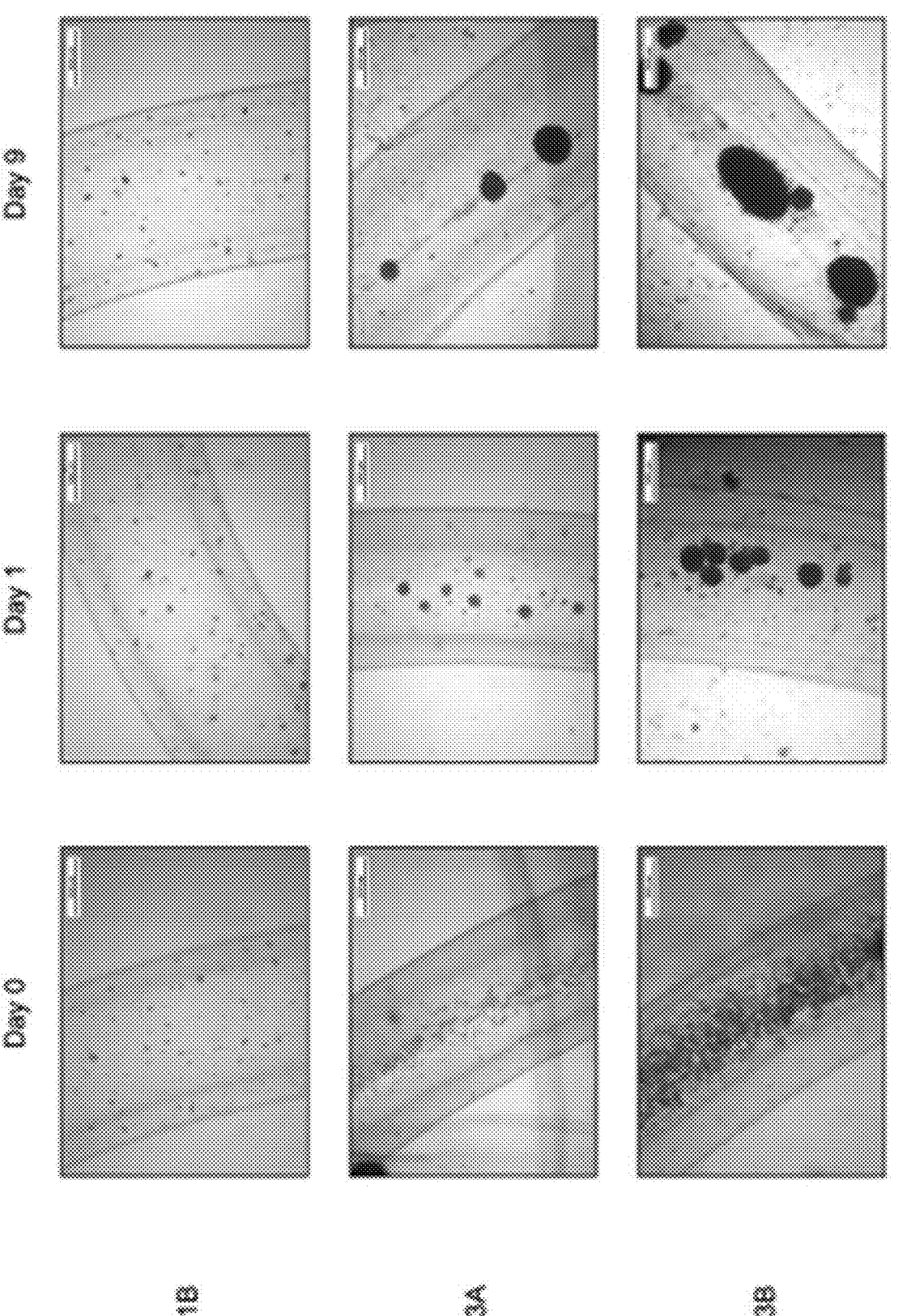
FIG. 16 depicts induction of lentoid formation using lens epithelial cells combined with FGF2-Stembeads in hydrogel microbeads made of 3% autoclaved alginate.

FIG. 16 depicts the feasibility of inducing lentoid formation using lens epithelial cells combined FGF2-Stembeads in hydrogel microbeads made of 3% autoclaved alginate. The three sub-figures of FIG. 16 (e.g., FIG. 16-1B, FIG. 16-3A, and FIG. 16-3B) depict snapshots in time at Day 0, Day 3, and Day 9. FIG. 16-1B shows a microtube with a shell containing $1 \times 10^6$ cells/mL and containing 8 μL FGF2-Stembeads within the lumen. FIG. 16-3A shows a microtube with 8 μL FGF2-Stembeads within the shell and $1 \times 10^6$ cells/mL within the lumen. FIG. 16-3B shows a microtube with 8 μL FGF2-Stembeads within the shell and $10 \times 10^6$ cells/mL within the lumen.

Needle-In-Needle Apparatus to Form a String of Microbubbles

Figure 17:
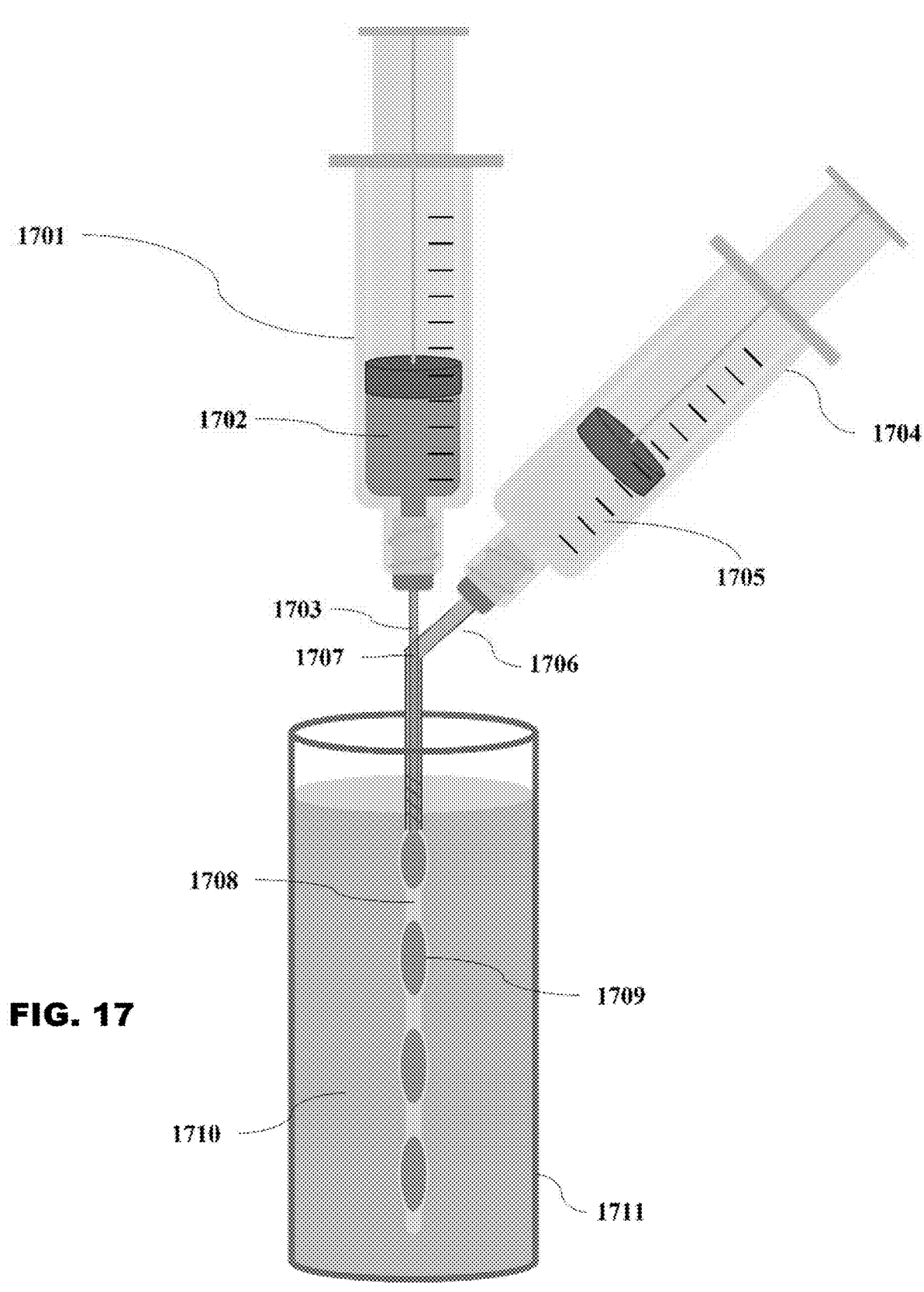
FIG. 17 is a diagram showing production of a string of microbubble structures using the needle-in-needle apparatus of the present disclosure.

FIG. 17 depicts a needle-in-needle apparatus to form a string of micro-bubbles. In the present embodiment, the apparatus consists of a first reservoir and a second reservoir to create a string of micro-bubbles within a third reservoir.

The first reservoir 1701 contains a cross-linking agent 1702. In the present embodiment, the cross-linking agent 1702 of the first reservoir 1701 is a CaCl₂) solution.

The second reservoir 1704 contains a hydrogel agent 1705. In the present embodiment, the hydrogel agent 1705 of the second reservoir 1704 is an alginate solution.

The third reservoir 1711 contains a cross-linking agent 1710. In the present embodiment, the cross-linking agent 1710 of the third reservoir 1711 is a CaCl₂) solution.

The first reservoir 1701 is connected to a first needle 1703. The second reservoir 1704 is connected to a second needle 1706. The first needle 1703 and the second needle 1706 are connected via an adapter 1707. The connection between the first needle 1703 and the second needle 1706 enables the contents of the first reservoir 1701 to be mixed, in pre-determined amounts, with the contents of the second reservoir 1704.

The needle-in-needle apparatus creates an outside flow of the hydrogel agent 1705 in the second needle 1706. In the present embodiment, the alginate flow is pre-determined.

The needle-in-needle apparatus creates an inside flow of the cross-linking agent 1702 in the first needle 1703. In the present embodiment, the CaCl₂) flow is pre-determined.

Specific intervals of high outflow pressure enable "stop and go" injection of the CaCl₂) solution to create microbubbles 1709 within the strand 1708. The strand of micro-bubbles is deposited/collected in the third reservoir 1711.

In the present embodiment, the cross-linking agent 1702 of the first reservoir (e.g., CaCl₂) solution within the first reservoir 1701) is at a lower concentration than the cross-linking agent 1710 of the third reservoir 1711 (e.g., the CaCl₂) solution within the third reservoir 1711).

Alternatively, one or more embodiments may include a hydrogel agent other than an alginate solution. As a further alternative embodiment, one or more embodiments may include a cross-linking agent other than a CaCl₂) solution. As yet a further alternative embodiment, one or more organic materials may be mixed with the hydrogel agent employed. As yet a further alternative embodiment, one or more organic materials may be mixed with the cross-linking agent employed.

Figure 18A:
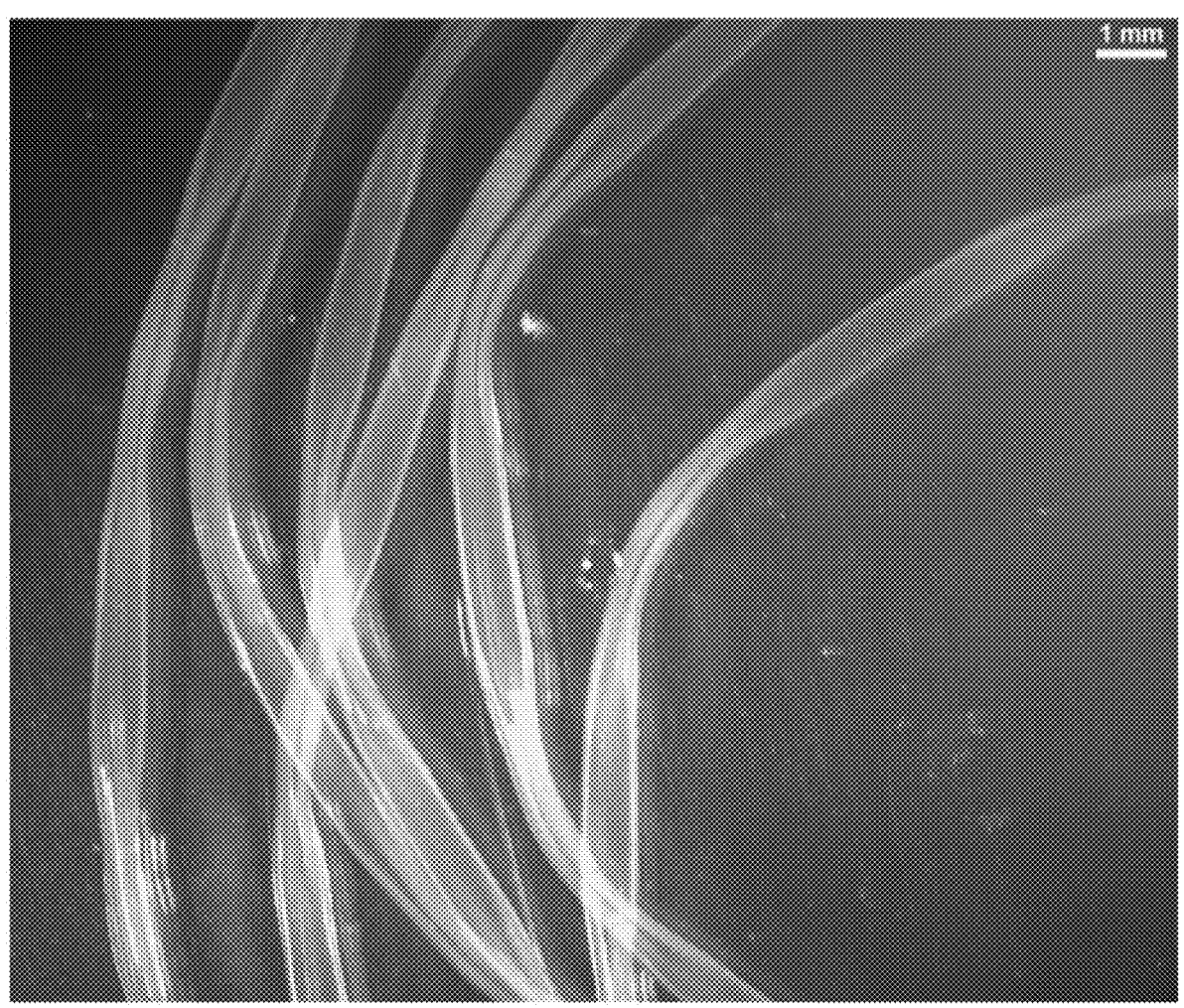
FIGS. 18A and 18B depict sample structures of a string of alginate hydrogel microbubbles.
Figure 18B:
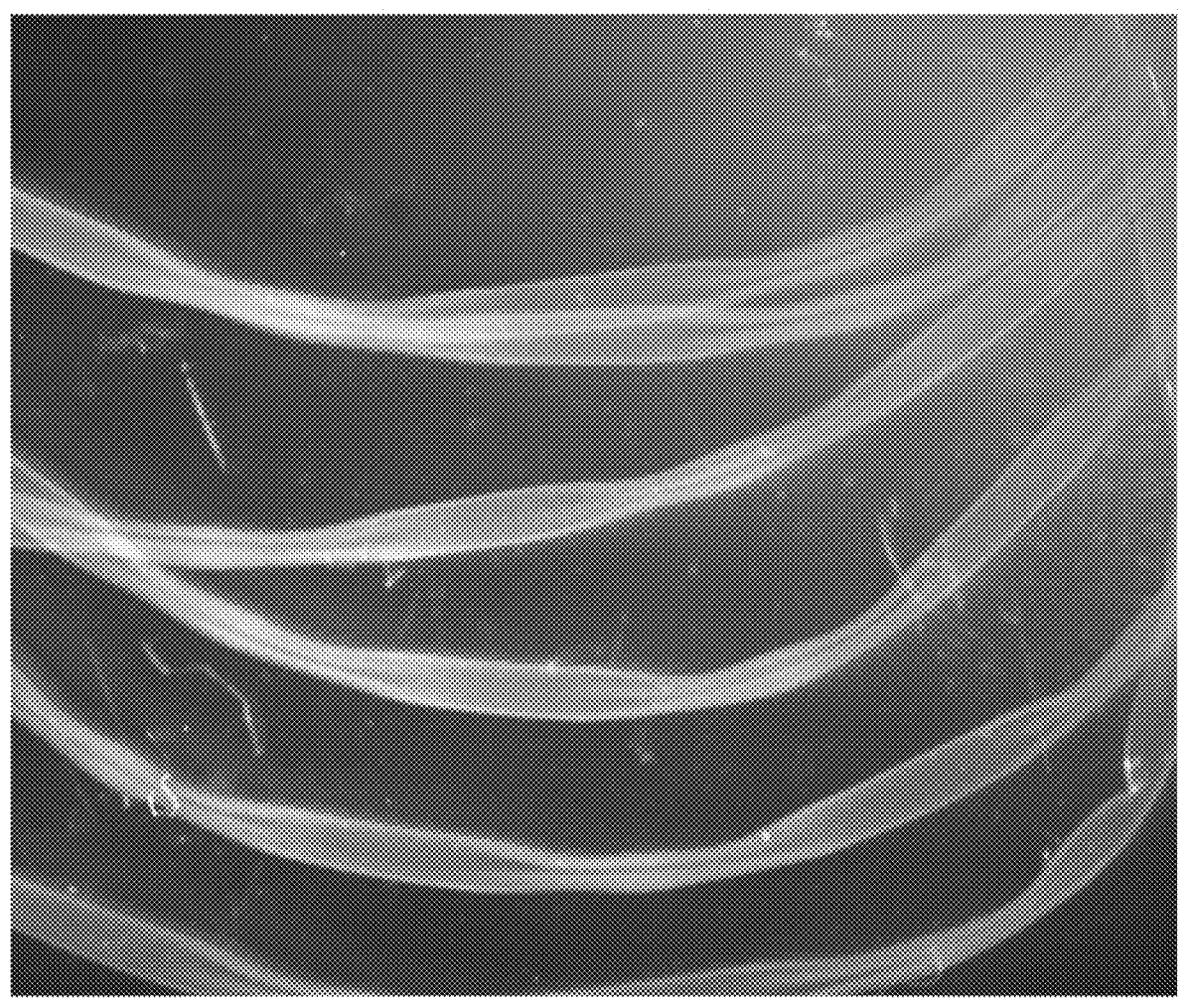

FIG. 18 depicts sample structures of a string of microbubbles that are formed as a result of the needle-in-needle apparatus described in FIG. 17. The micro-bubbles depicted in FIG. 18 are empty. That is, the micro-bubbles depicted in FIG. 18 are filled with air.

Additional Embodiments

In some embodiments the present disclosure relates to a method for organoid structure formation including: providing an apparatus including: at least two connected reservoirs; a first reservoir that contains a first substance; a second reservoir that contains a second substance; wherein the apparatus is configured for pull technique on at least one of the reservoirs to create a vacuum. In embodiments, the first reservoir contains calcium chloride and/or a derivative of calcium chloride. In embodiments, the second reservoir contains alginate. In embodiments, the second reservoir contains alginate and at least one of the following substances, selected from: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; (xvii) vaccines, and combinations thereof. In embodiments, the second reservoir includes: alginate and cells, alginate and tissues, alginate and organoids, alginate and micro-organisms, or alginate and virus, alginate and macromolecules, alginate and proteins, alginate and DNA, alginate and RNA, alginate and lipids, alginate and polysaccharides, alginate and exosomes, alginate and biocatalysts, alginate and pharmacological agents, alginate and drugs, alginate and genes, alginate and vaccines. In embodiments, the lentoid is spherical, or substantially spherical.

In some embodiments, the present disclosure relates to a microtube product made by a process including the steps of: filling a first reservoir with a crosslinking agent; filling a second reservoir with a hydrogel agent; connecting the first reservoir to the second reservoir; creating a vacuum within the first and second reservoir based, at least in part, on a pulling motion of the first reservoir; transferring, either in part or in whole, the hydrogel agent of the second reservoir into the crosslinking agent of the first reservoir. In embodiments, the second reservoir contains an alginate solution of 6%, or an alginate solution of 3%. In embodiments, the second reservoir contains a solution of any composition and of any concentration that can be converted to hydrogel by withdrawing it into the crosslinking solution. In embodiments, the hydrogel agent of the second reservoir contains alginate and at least one of the following substances, including: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; and (xvii) vaccines. In embodiments, the hydrogel agent of the second reservoir contains a solution that can be crosslinked to form a hydrogel by the use of a crosslinking agent and at least one of the following substances, including: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; and (xvii) vaccines. In embodiments, the second reservoir contains alginate and cells, alginate and tissues, alginate and organoids, alginate and micro-organisms, alginate and virus, alginate and macromolecules, alginate and proteins, alginate and DNA, alginate and RNA, alginate and lipids, alginate and polysaccharides, alginate and exosomes, alginate and biocatalysts, alginate and pharmacological agents, alginate and drugs, alginate and genes, alginate and vaccines. In embodiments, the first reservoir includes $CaCl_2$). In embodiments, the first reservoir includes a crosslinking solution. In embodiments, the first reservoir includes polylysine. In embodiments, the first reservoir contains, at least in part, $CaCl_2$) and polylysine. In embodiments, the first reservoir is a syringe. In embodiments, the first reservoir is a container that enables tight closure to obtain high vacuum within the container. In embodiments, the second reservoir is a syringe. In embodiments, the second reservoir is a closed container that has a movable piston that has a similar mechanism of action to that of a syringe. In embodiments, the process may further include one or more of the following features, including: (i) the first reservoir is a syringe; (ii) the second reservoir is a syringe; (iii) the diameter of the first reservoir syringe is larger than the diameter of the second reservoir syringe; (iv) the first reservoir syringe and the second reservoir syringe are connected via an adapter; (v) the second reservoir syringe is inserted into the first reservoir syringe; (vi) the plunger of the first reservoir syringe is pulled to create a vacuum; (vii) the plunger of the first reservoir syringe is pulled to create a vacuum to draw one or more units a hydrogel agent in the second reservoir into the first reservoir; (viii) two reservoirs of any diameter; (ix) the needle from a first syringe into a second syringe with the aid of an adapter; (x) the diameter of the first reservoir syringe is smaller than the diameter of the second reservoir syringe; and (xi) the diameter of the first reservoir syringe is equal to the diameter of the second reservoir syringe. In embodiments, a filter is added at the inlet of the first reservoir to determine the geometric configuration of the one or more units of hydrogel agent that is drawn from the second reservoir.

In some embodiments, the present disclosure relates to a device to for forming one or more micro-strands, including: a first reservoir including a crosslinking agent; a second reservoir including a hydrogel agent; an adapter to connect the first reservoir and a second reservoir; a mechanical component to create a vacuum within the first reservoir to transfer one or more units of the hydrogel agent within the second reservoir to the first reservoir. In embodiments, the first reservoir is a syringe. In embodiments, the second reservoir is a syringe. In embodiments, the device further includes: (i) the first reservoir as a syringe; (ii) the second reservoir as a syringe; (iii) the first reservoir syringe has a larger gauge than the second reservoir syringe; and (iv) the second reservoir syringe is inserted into the first reservoir syringe via an adapter. In some embodiments; (ii) the second reservoir is a syringe; (iii) the two syringes are of similar gauges, and the needle gauge is varied; and (iv) the needle of the second reservoir syringe that contains the alginate is inserted into the first reservoir syringe via an adapter. In some embodiments, the first reservoir includes a crosslinking agent such as $CaCl_2$) solution. In embodiments, the second reservoir includes a hydrogel agent which is an alginate solution. In embodiments, the hydrogel agent of the second reservoir is an alginate solution with an alginate concentration of 6%, or 3%. In embodiments, the hydrogel agent is an alginate solution which contains alginate with a concentration of 6% and one or more of the following materials, including: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; and (xvii) vaccines. In embodiments, the hydrogel agent is an alginate solution which contains alginate with a concentration of 3% and one or more of the following materials, including: (i) cells; (ii) tissues; (iii) organoids; (iv) micro-organisms; (v) virus; (vi) macromolecules; (vii) proteins; (viii) DNA; (ix) RNA; (x) lipids; (xi) polysaccharides; (xii) exosomes; (xiii) biocatalysts; (xiv) pharmacological agents; (xv) drugs; (xvi) genes; and (xvii) vaccines. In embodiments, the device includes a mechanical component such as a plunger. In embodiments, the crosslinking agent is a $CaCl_2$) solution, or a solution of $CaCl_2$) and polylysine. In embodiments, the first reservoir is a syringe and the second reservoir is a syringe, and the first reservoir syringe has a larger gauge than the second reservoir syringe. In embodiments, the device includes an adapter that measures flow rate. In embodiments, the adapter controls flow rate. In embodiments, the adapter measures pressure. In embodiments, the adapter controls pressure. In embodiments, the adapter measures and/or controls the flow rate. In embodiments, the adapter tightly seals the containers or reservoirs or syringes, to enable the creation of a vacuum inside the first container or reservoir or syringe, when the plunger is pulled or when the vacuum is turned on. In embodiments, the device further includes one or more of the following features: (i) measuring flow rate; (ii) changing flow rate; (iii) measuring pressure; (iv) changing pressure; (v) measuring flow rate of the hydrogel agent in the second reservoir; (vi) changing flow rate of the hydrogel agent in the second reservoir as the hydrogel agent flows to the first reservoir; (vii) measuring pressure within the first reservoir; (viii) measuring pressure within the second reservoir; (ix) changing pressure within the first reservoir; (x) changing pressure within the second reservoir; and (xi) measuring the vacuum within the first reservoir.

In embodiments, the present disclosure relates to a device for the formation of micro-strands, including: a first reservoir; a second reservoir; a vacuum pump; and an adapter. In embodiments, the first reservoir is a syringe. In embodiments, the second reservoir is a container. In embodiments, the first reservoir is connected horizontally to the second reservoir. In embodiments, a vacuum pump is connected vertically to the second reservoir. In embodiments, the first reservoir is connected to the second reservoir via a vacuum sealed adapter. In embodiments, the device further includes one or more of the following or is configured for: (i) connecting a first reservoir horizontally to a second reservoir via an adapter; (ii) connecting a vacuum pump to the second reservoir vertically; (iii) controlling the vacuum pressure applied to the apparatus; (iv) monitoring the vacuum pressure applied to the apparatus; (v) adjusting the vacuum pressure applied to the apparatus; (vi) transferring the contents of a first reservoir to a second reservoir by vacuum pressure applied vertically to the second reservoir; and (vii)

filtering the contents of the first reservoir as the contents are transferred to the second reservoir via a porous filter to create one or more micro-strands within the second reservoir.

Kits

Embodiments of the present disclosure provides for easy-to-use multi-part kit systems for the preparation of one or more microfibers, microstrands, tubules, or 3D structures in accordance with the present disclosure. In embodiments, a multipart kit system comprising one or more syringes, needles, conduits, or reagents for use in accordance with the present disclosure may be combined a single or multiuse kit. In some embodiments, a kit, such as a 3D cell culture kit may include the different parts depending upon need. For example, a syringe-in-syringe strategy (as shown in FIGS. 1A and 1B), may include one or more of: alginate solution, calcium solution, 2 syringes, and one conduit configured to attach between the 2 syringes. Optionally, the kit may include 2 sampling needles. In embodiments, the kit may include an adapter for attaching the conduit and one or more syringes.

In another embodiment, such as for Syringe-in-Syringe with Needle-in-Needle approach, a kit may include one of more of alginate solution, calcium solution, 3 syringes, 3 sampling needles, and one needle-in-needle device that can be attached to three needles.

In embodiments, a kit may include the components and features suitable for forming the apparatus of FIG. 1A, FIG. 1B, FIG. 3, FIG. 5D, FIG. 5E, FIG. 7, FIG. 11, alone, or in combination. In embodiments, any of the components described herein above may be combined together to form a kit suitable cell culture and forming 3D structures in accordance with the present disclosure.

The claimed subject matter below is, of course, not necessarily limited to one of the embodiments described herein. In the preceding description, various aspects of claimed subject matter have been described. For purposes of explanation, specific numbers, systems, or configurations may have been set forth to provide a thorough understanding of claimed subject matter. However, it should be apparent to one skilled in the art having the benefit of this disclosure that claimed subject matter may be practiced without those specific details.

In other instances, features that would be understood by one of ordinary skill may have been omitted or simplified so as not to obscure the claimed subject matter. While certain features have been illustrated, or described herein, many modifications, substitutions, changes, or equivalents may now occur to those skilled in the art. It is, therefore, to be understood that the appended claims are intended to cover all such modifications or changes as fall within the true spirit of claimed subject matter.

What is claimed is:

1. An apparatus for forming microfibers, comprising:
a first reservoir containing a first crosslinking agent;
a second reservoir containing a hydrogel agent;
an adapter connecting the first reservoir and a second reservoir, the adapter fluidly coupling the first reservoir and the second reservoir, the adapter configured to form microfibers from the hydrogel agent being drawn therethrough;
a mechanical component to create negative pressure within the first reservoir to draw one or more units of the hydrogel agent within the second reservoir through the adapter to the first reservoir to thereby create microfibers; and at least one conduit in fluid communication between the first reservoir and second reservoir, the conduit further comprising a first needle, second needle, and third needle, the third needle attached to the adapter, wherein the first needle, second needle, and third needle are in fluid communication the at least one conduit, and the conduit further in fluid communication with a third reservoir comprising one or more second crosslinking agents.

2. The apparatus of claim 1, wherein the first reservoir and second reservoir are syringes.

3. The apparatus of claim 2, wherein the second reservoir including a syringe and a plunger configured such that when pulled away from the adapter, a negative pressure formed within the second reservoir.

4. The apparatus of claim 1, further comprising positioning a filter in an opening of the conduit, wherein the filter comprises a plurality of holes.

5. The apparatus of claim 1, wherein the hydrogel agent is an alginate solution with an alginate concentration of 1-20%.

6. The apparatus of claim 1, wherein the crosslinking agent is one or more from a group comprised of: N-hydroxysuccinimide (NHS), ethyl dimethylaminopropyl carbodiimide (EDC), and calcium chloride dihydrate.

7. The apparatus of claim 1, wherein the first needle and second needle are in a gauge in a range of 10 gauge to 34 gauge.

8. A device for forming one or more organoid structures, comprising:
a first reservoir containing a first crosslinking agent;
a second reservoir containing a hydrogel agent containing organoids;
a negative pressure device; and
an adapter fluidly coupling the first reservoir and the second reservoir, the adapter configured to form organoid-laden structures from the hydrogel agent being drawn therethrough, wherein the negative pressure device is configured to draw hydrogel agent from the first reservoir through the adapter to the second reservoir; and
at least one conduit in fluid communication between the first reservoir and second reservoir, the third needle attached to the adapter, wherein the first needle, second needle, and third needle are in fluid communication the at least one conduit, and the conduit further in fluid communication with a third reservoir comprising one or more second crosslinking agents.

9. The device of claim 8, wherein the conduit comprises a first needle extending from the first reservoir to the second reservoir, wherein the second reservoir is disposed within a syringe having a distal opening, and wherein the adapter is disposed around the first needle and within the distal opening.

10. The device of claim 8, wherein the adapter is disposed over and atop a first needle and a second needle.

11. The device of claim 8, wherein the conduit has an opening, and further comprising a filter in an opening of the conduit, the filter including a plurality of holes.

12. The device of claim 8, wherein the first reservoir is disposed within a first syringe and the second reservoir is disposed within a second syringe.

13. The device of claim 8, wherein negative pressure device creates a negative pressure between 250 Torr to 650 Torr.

14. An apparatus for forming microfibers, comprising:
a first reservoir containing a first crosslinking agent;

a second reservoir containing a hydrogel agent;

a forming means for forming microfibers from the hydrogel agent being drawn therethrough, the forming means further fluidly coupling the first reservoir and a second reservoir; and a mechanical means for creating a negative pressure within the first reservoir to draw one or more units of the hydrogel agent within the second reservoir through the forming means to the first reservoir; and at least one conduit in fluid communication between the first reservoir and second reservoir, the conduit further comprising a first needle, second needle, and third needle, the third needle attached to the forming means, wherein the first needle, second needle, and third needle are in fluid communication the at least one conduit, and the conduit further in fluid communication with a third reservoir comprising one or more second crosslinking agents.

* * * * *